(12) United States Patent
Wise et al.

(10) Patent No.: US 6,423,045 B1
(45) Date of Patent: Jul. 23, 2002

(54) DISPOSABLE GARMENT HAVING AN EXPANDABLE COMPONENT

(75) Inventors: Brandon E. Wise; Kimberly A. Dreier; Mark J. Kline; Constance L. Fisher, all of Cincinnati; Tracey E. Beckman, Greenhills; Donald C. Roe, West Chester, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/481,042

(22) Filed: Jan. 11, 2000

(51) Int. Cl.$^7$ ................................................ A61F 13/15
(52) U.S. Cl. ........................ 604/385.12; 604/385.01; 604/379; 604/380
(58) Field of Search .......................... 604/385.12, 379, 604/380, 385.01

(56) References Cited

U.S. PATENT DOCUMENTS

| | | | |
|---|---|---|---|
| 3,512,528 A | 5/1970 | Whitehead et al. | 128/285 |
| 3,921,232 A | 11/1975 | Whyte | 5/91 |
| 4,781,645 A | 11/1988 | Kato | 446/188 |
| 4,828,556 A | * 5/1989 | Braun et al. | 604/365 |
| 4,929,214 A | 5/1990 | Liebermann | 446/221 |
| 5,306,266 A | 4/1994 | Freeland | 604/385.1 |
| 5,330,459 A | 7/1994 | Lavon et al. | 604/385.1 |
| 5,520,674 A | * 5/1996 | Lavon et al. | 604/385.1 |
| 5,876,393 A | 3/1999 | Ahr et al. | 604/387 |
| 5,997,520 A | 12/1999 | Ahr et al. | 604/385.1 |
| 6,180,847 B1 | * 1/2001 | Ahr et al. | 604/367 |

FOREIGN PATENT DOCUMENTS

DE  3517192 A1  11/1986  ........... A61F/13/16

* cited by examiner

Primary Examiner—John G. Weiss
Assistant Examiner—Jacqueline F Stephens
(74) Attorney, Agent, or Firm—Michael P. Hayden; David M. Weirich; Ken K. Patel

(57) ABSTRACT

A disposable garment having a consumer-activated component that is expandable to improve the fit and function of the garment. The expandable component includes a compressed, resilient, expansible member disposed within a sealed, air-impermeable envelope. The expandable component can be activated so that the component expands in a direction toward the body of the wearer of the garment by the application of a tensile force on the garment to expose an opening in the envelope, to thereby admit air into the envelope and allow the compressed expansible element to expand to its substantially uncompressed condition. When expanded, the expansible element can define a collection chamber for waste matter, or it can provide closer contact between the garment and the body of the wearer at predetermined areas to improve the fit of the garment to the body of the wearer, or it can provide closer contact between the garment and the body of the wearer to position an absorptive member adjacent a body opening to improve the absorption by the absorptive member of waste bodily fluids. The garment can thus be a disposable diaper, a sanitary napkin, or the like.

38 Claims, 6 Drawing Sheets

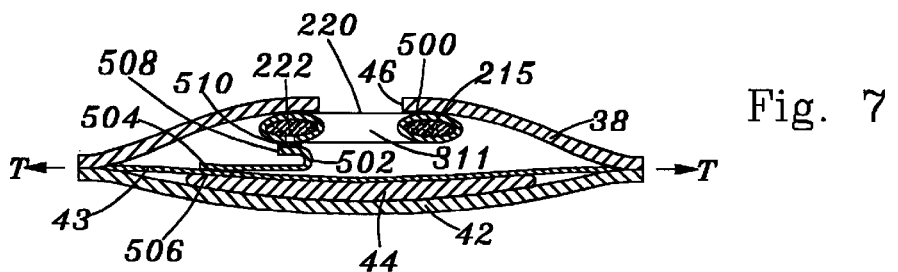
Fig. 7
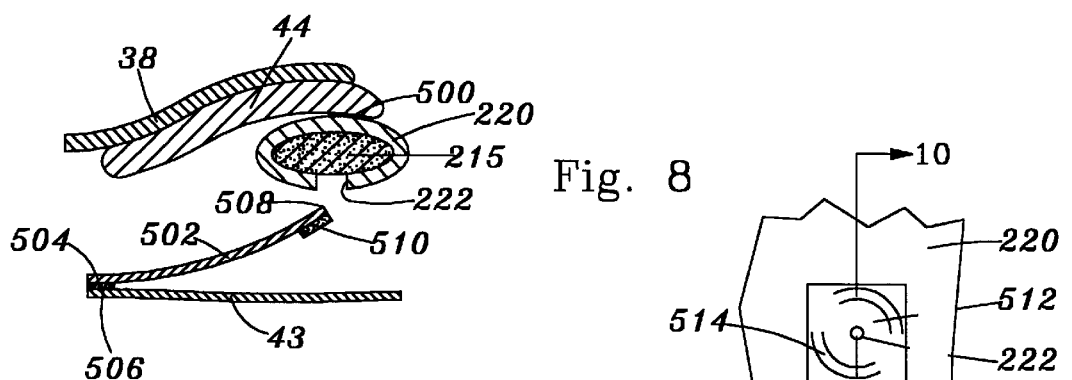
Fig. 8
Fig. 9
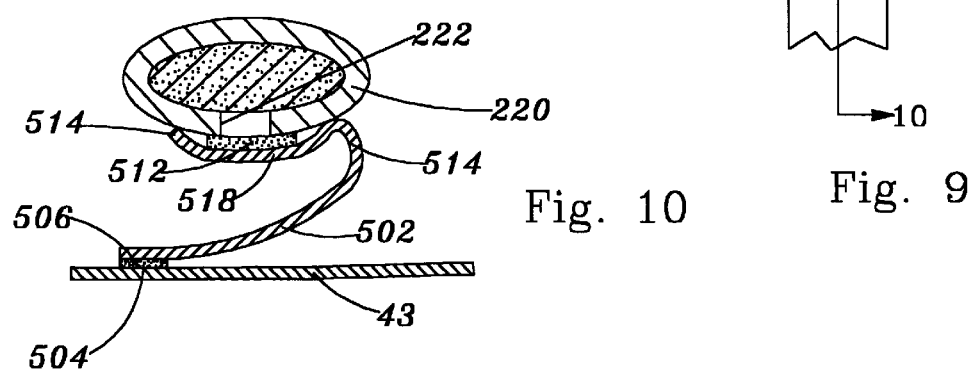
Fig. 10
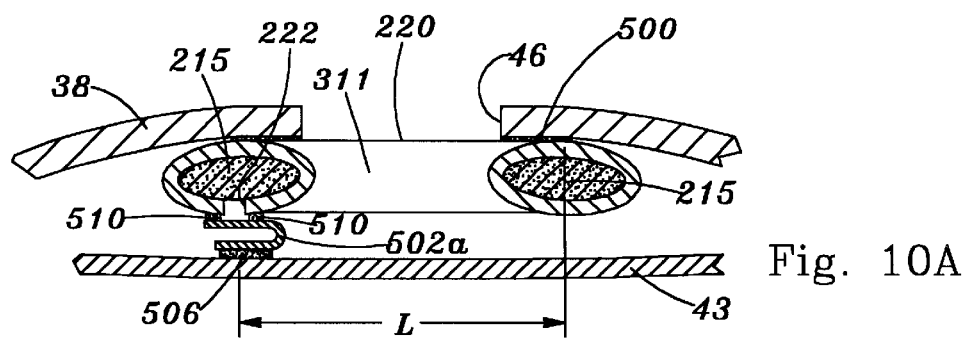
Fig. 10A

DISPOSABLE GARMENT HAVING AN EXPANDABLE COMPONENT

FIELD OF THE INVENTION

The present invention relates to a disposable garment having a consumer-activated component that is expandable to improve the fit and function of the garment. More particularly, the present invention relates to a disposable garment that includes one or more elements that are initially in a relatively flat, compressed form and that are subsequently allowed to expand by the application of tension to the garment at or shortly before the time the garment is applied to body of the wearer.

BACKGROUND OF THE INVENTION

Garments in the form of disposable absorbent articles are provided to absorb and to retain body exudates, such as urine, fecal material, menses, and the like. A particularly desired feature of such disposable absorbent articles is the ability to acquire and to hold body exudates to minimize leakage of the exudates from between the garment and the wearer. Another desired feature of such articles is that they conform with and fit the body of the wearer in such a way that they are retained in a desired wearing position as the wearer's body moves.

It is known to add to a disposable absorbent article a pre-formed spacer for providing a collection space for containing fecal material. However, such pre-formed spacers suffer from the disadvantage that they have an initial thickness that causes an increase in the thickness of the article, and therefore articles including such spacers are thicker and occupy more space within a package, which increases shipping and storage costs as compared with disposable absorbent articles that do not include such spacers. Additionally, such spacers can also be perceived by consumers to be uncomfortable to a wearer because of their thickness at the time of application of the article to a wearer, and they can also be perceived to adversely affect the fit of the wearer's outer clothing.

Various forms of known spacers for use in connection with disposable absorbent articles are illustrated and described in the following patents: U.S. Pat. No. 5,520,674, entitled "Disposable Absorbent Article Having a Sealed Expandable Component," which issued on May 28, 1996, to Lavon et al.; U.S. Pat. No. 5,176,672, which issued on Jan. 5, 1993, to Bruemmer et al.; U.S. Pat. No. 5,171,236, which issued on Dec. 15, 1992, to Dreier et al.; and U.S. patent application Ser. No. 07/898,047, entitled "Spacers for Use in Disposable Absorbent Articles and Disposable Absorbent Articles Having Such Spacers," filed Jun. 11, 1992, by Allen et al. It is noted that a continuation of application Ser. No. 07/898,047 was filed as application Ser. No. 08/698,471 on Aug. 15, 1996 and matured into U.S. Pat. No. 6,168,584 issued on Jan. 2, 2001.

A disclosure of an absorbent article having an inflatable structure is contained in French Patent Application 2,561,078, published Sep. 20, 1985, in the name of Lefebvre. A diaper is disclosed having a structural element that is inflatable by mouth. However, inflation can be awkward or inconvenient to perform, especially in public areas or at a time when the diaper is already fastened to a wearer. Further, such an inflation arrangement is also undesirable because of sanitary considerations.

U.S. Pat. Nos. 3,881,491 and 3,921,232, which issued to Whyte on May 6, 1975, and Nov. 25, 1975, respectively, disclose disposable absorbent articles having self-inflating structures. The structures have a wall of semipermeable material through which body fluids can pass, and include a gas-evolving material that interacts with an activator material (e.g., urine) to inflate the structures. However, the structures taught by Whyte primarily prevent core densification, and they suffer from the disadvantage that they require an activator material from an external source, such as urine, and the wearer may not urinate at the desired time, in the desired location, or in the desired quantity to properly inflate the structure.

U.S. patent application Ser. No. 08/081,733 filed Jun. 23, 1993 in name of Ahr et al. and Ser. No. 08/081,536 filed Jun. 23, 1993 in name of LaVon et al. disclose inflatable diaper components whose inflation requires wetting of a component or of a mixture of two different materials. It is noted that a continuation of application Ser. No. 08/081,733 was filed as Application Ser. No. 08/422,676 on Apr. 13, 1995 and matured into U.S. Pat. No. 6,180,847 issued on Jan. 30, 2001. It is also noted that application Ser. No. 08/081,536 matured into U.S. Pat. No. 5,330,459 issued on Jul. 19, 1994.

Accordingly, it would be desirable to provide a disposable garment having a component that is expandable at or shortly after the time the garment is applied to the body of a wearer, to improve the fit and function of the garment. It would also be desirable to provide a disposable diaper having a spacer for providing a fecal matter collection space, wherein the thickness of the spacer can be increased without the need for wetting of the spacer, and wherein the spacer thickness can be increased by the consumer or the wearer. It would also be desirable to provide a sanitary napkin having a component that is expandable at the point of use of the sanitary napkin to provide separation and lift of the napkin topsheet and core relative to the backsheet of the sanitary napkin, and thereby provide increased caliper of the sanitary napkin along its longitudinal centerline.

Further, it would be desirable to provide a disposable absorbent article having an expandable component including a compressed resilient element that is disposed in an air impermeable envelope for delayed expansion, wherein most of the expansion occurs after the article has been removed from a package and has been applied to the body of a wearer.

SUMMARY OF THE INVENTION

Briefly stated, in accordance with one aspect of the present invention, a disposable garment is provided that includes first and second structural elements that form part of the garment body. An envelope is carried between the first and second structural elements, wherein the envelope is in sealed condition and contains a compressed spacer element. The envelope is securely connected with the first structural element at a first retention point. An activator is connected with the envelope and extends from the envelope to the second structural element at a second retention point. Upon the application of tension to the garment the first and second retention points move away from each other and the activator opens a flow passageway into the envelope to allow the spacer element to expand from its compressed condition to a substantially uncompressed condition.

In accordance with another aspect of the present invention, a disposable garment is provided that includes a garment body. A formed, resilient, expansible member is carried by the garment body and is positioned to be adjacent the body of a wearer when the garment is worn. The expansible member is initially in at least a partially compressed condition within an envelope. The envelope is attached to the garment body at a first retention point, and it is in a sealed condition about the at least partially compressed expansible member so that the expansible member is maintained in an at least a partially compressed condition until an opening is provided in the envelope to admit ambient air therein. An activator is carried by the garment and is connected with the envelope at a first activator connection point. The activator is also connected with a portion of the garment body at a second activator connection point that defines a second retention point that is spaced from the first retention point by a region of the garment body. Upon the application of a tensile force to the garment to extend the region of the garment body that is between the first retention point and the second retention point, the activator opens a flow passageway in the envelope adjacent to the first activator connection point to admit ambient air into the envelope and thereby allow the expansible member to decompress and to expand from its initial at least partially compressed condition to a substantially uncompressed condition.

In accordance with another aspect of the present invention the garment is a disposable diaper and the expansible member defines a collection chamber for collecting fecal matter.

In accordance with a further aspect of the present invention the garment is a disposable diaper and the expansible member is disposed in a waist region of the diaper to improve the fit of the diaper about the waist of the wearer.

In accordance with a still further aspect of the present invention the garment is a disposable diaper and the expansible member is disposed in a marginal area of the diaper to improve the fit of the diaper about the legs of the wearer.

In accordance with another aspect of the present invention the garment is a sanitary napkin and the expansible member is disposed along the longitudinal axis of the napkin to improve its function.

BRIEF DESCRIPTION OF THE DRAWINGS

FIG. 7 is a longitudinal, cross-sectional view similar to that of FIG. 3, showing an embodiment of the present invention in which an activator strip is provided within the garment structure to permit opening of the expandable component envelope.

FIG. 8 is an enlarged, fragmentary, cross-sectional view showing the expandable component envelope of FIG. 7 immediately after the activator has been separated from the envelope.

FIG. 9 is an enlarged, fragmentary view of a portion of an expandable-component-containing envelope, showing a semi-permeable membrane and an activator overlying and covering an air-admission aperture provided in a wall of the expandable component envelope.

FIG. 10 is an enlarged, fragmentary, cross-sectional view taken along the line 10—10 of FIG. 9.

DETAILED DESCRIPTION OF THE INVENTION

As used herein, the term "garment" refers to absorbent articles that absorb and contain body exudates, and, more specifically, it refers to absorbent articles that are placed against or in proximity to the body of a wearer to absorb and contain various exudates discharged from the body. Such absorbent articles include, but are not limited to, diapers, training pants, incontinence briefs, diaper holders, diaper liners, and the like. Also includes within the term "garment" are feminine hygiene products, such as sanitary napkins, pantiliners, and the like.

As used herein in connection with disposable articles, the term "disposable" refers to absorbent articles that are not intended to be laundered or otherwise restored or reused as an absorbent article (i.e., they are intended to be discarded after a single use and, preferably, to be recycled, composited, or otherwise disposed of in an environmentally compatible manner).

Figure 1:
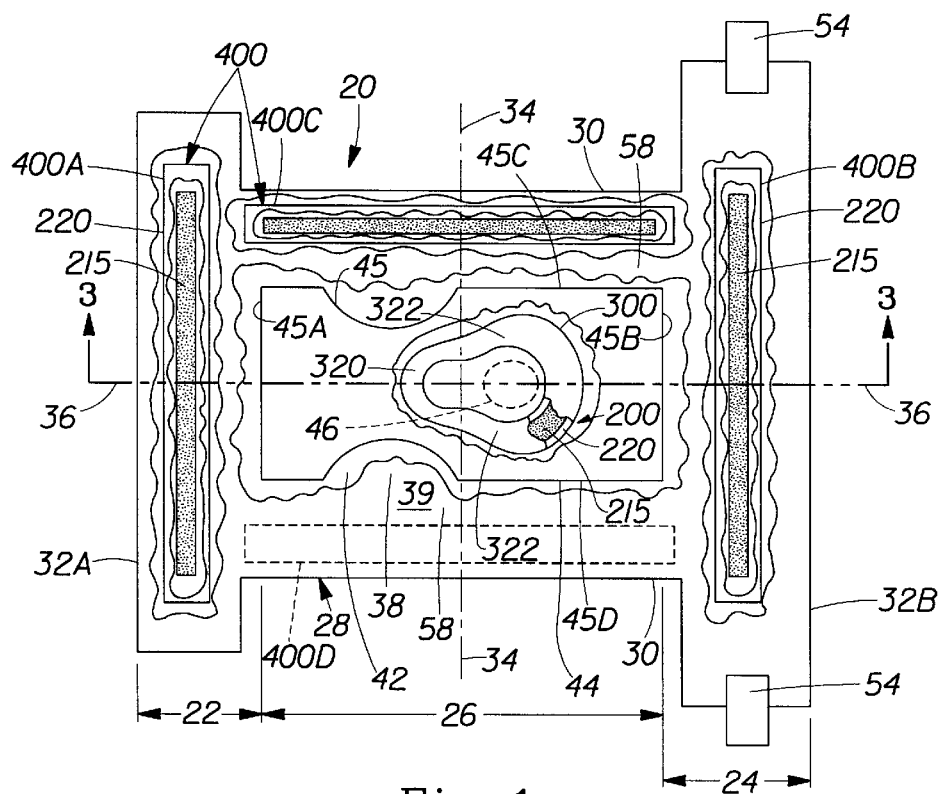
FIG. 1 is a top plan view of a garment in the form of a disposable diaper, with portions of the structure broken away to illustrate the positions of expandable components, including a centrally-positioned, ring-like expandable component for providing a collection space for fecal matter, and including expandable components positioned at the waist regions and at the side margins of the garment.

One embodiment of an absorbent article in accordance with the present invention is the unitary disposable diaper 20 shown in FIG. 1. As used herein, the term "diaper" refers to an absorbent article that is worn about the lower torso, generally by infants and other incontinent persons. FIG. 1 is a plan view of a diaper 20 in accordance with the present invention in its flat-out, uncontracted state (i.e., with all elastically-induced contractions fully extended) and with portions of the structure broken away to more clearly show the internal construction of diaper 20. As viewed in FIG. 1, the face of diaper 20 that faces or contacts the wearer, the inner, body-facing surface, faces the viewer of that drawing figure.

Diaper 20 as shown in FIG. 1 has a front waist region 22, a rear waist region 24, a crotch region 26, and a periphery 28 that includes a pair of laterally-spaced longitudinal edges 30 and a pair of longitudinally-spaced front and rear lateral end edges 32A and 32B, respectively. (It should be noted that the terms "front waist region" and "rear waist region" as used herein can be interchanged unless otherwise designated and thus, the present invention contemplates embodiments wherein the front waist region of the diaper can be placed across the rear waist of a wearer and the rear waist region can be placed across the front waist of a wearer.) Diaper 20 also has a lateral centerline 34 and a longitudinal centerline 36.

As used herein, the term "longitudinal" as applied to a dimension, direction, or axis of diaper 20 is a dimension, direction, or axis that is aligned with or is parallel to longitudinal centerline 36. Similarly, the term "lateral" or "transverse" as applied to a dimension, direction, or axis of diaper 20 is perpendicular to the longitudinal direction and is aligned with or is parallel to lateral centerline 34. And "Z-direction" as used herein is a direction that is orthogonal to both the longitudinal and the transverse directions, and is identified in the cross sections shown in FIGS. 3 and 4.

Front waist region 22 and rear waist region 24 are those portions of diaper 20 that, when the outer ends thereof are connected with each other when the diaper is worn, at least partially cover the waist of a wearer. Crotch region 26 is disposed between the front and rear waist regions 22, 24 and is that part of diaper 20 that, when worn, passes between the wearer's legs.

Figure 2:
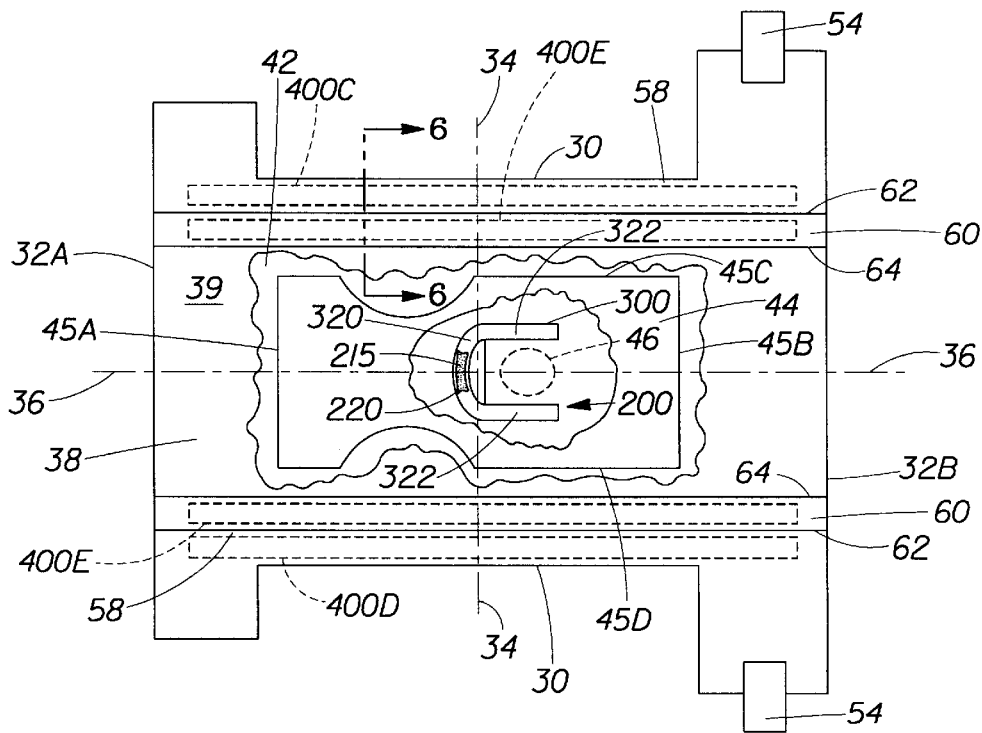
FIG. 2 is a top plan view of another disposable diaper, similar to that of FIG. 1, showing a centrally-positioned, U-shaped, expandable component.
Figure 3:
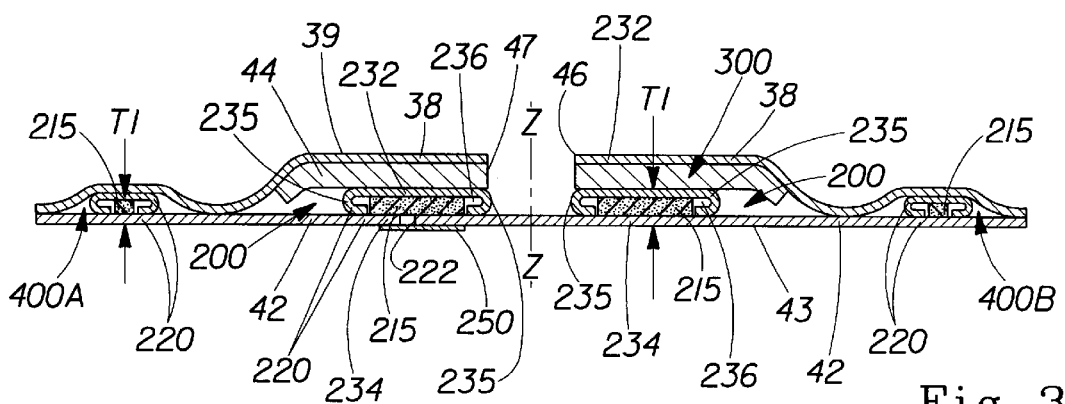
FIG. 3 is a cross-sectional view taken along the line 3—3 of FIG. 1, showing the expandable components of the diaper in an initial, compressed state.

As shown in FIGS. 1 through 3, diaper 20 includes a liquid-pervious topsheet 38 and a liquid-impervious backsheet 42 that is joined at least peripherally with topsheet 38. An absorbent core 44 is disposed between topsheet 38 and backsheet 42 and can include one or more layers of material, with only a single layer shown in the drawings. Absorbent core 44 has a perimeter 45 that includes front and rear laterally extending ends 45A and 45B, respectively, as well as side edges 45C and 45D. The core 44 may be disposed only in the crotch region or may extend into either or both waist regions 22 and 24.

Diaper 20 includes side margins 58 that extend laterally outwardly from absorbent core side edges 45C and 45D to longitudinal edges 30 of the diaper. Side margins 58 are defined by those portions of topsheet 38 and/or of backsheet 42 that extend laterally outwardly from at least a portion of the absorbent core side edges 45C and 45D.

Diaper 20 has a body-facing surface 39 that is defined by at least a portion of topsheet 38 and is positioned adjacent to the wearer's body when the diaper is worn. Diaper 20 also has a garment-facing surface 43 (see FIG. 3) that faces away from the wearer's body, that is defined by at least a portion of backsheet 42, and that can include components that are joined to backsheet 42.

Figure 4:
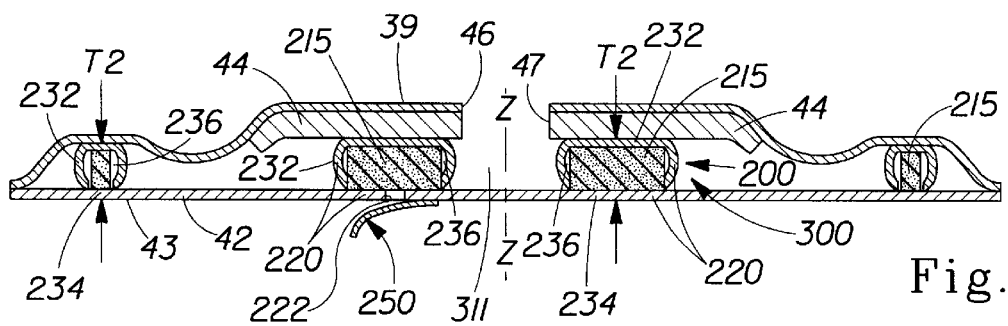
FIG. 4 is a cross-sectional view similar to that of FIG. 3, showing the expandable components of the diaper in a later, expanded state.

In one embodiment of the invention at least one expandable component 200 is carried within the diaper 20. Expandable component 20 is positioned relative to the diaper axes so that it is substantially centered in a transverse direction of the diaper and so that it is offset from the diaper center in a longitudinal direction of the diaper. Expandable component 200 is expandable from an initial, compressed condition, in which it has a first thickness T1 as shown in FIG. 3, to a final, expanded condition, in which it has a second thickness T2 as shown in FIG. 4.

Expandable component 200 includes a resilient element 215 that is disposed within a sealed, air-impermeable envelope 220 that has an opening or air access port 222 that is closed by a releasable closure 250, as shown in FIG. 3. Compressed resilient element 215 does not expand within sealed, air-impermeable envelope 220 because the interior of envelope 220 is in pressure equilibrium with the ambient atmosphere and such expansion would increase the volume within sealed air impermeable envelope 220, which would lower the air pressure within sealed envelope 220. Accordingly, the atmospheric pressure outside envelope 220 operates to prevent expansion of resilient element 215 within the envelope. Upon allowing air to enter impermeable envelope 220, such as by releasing closure 250 to permit air to enter through port 222, as shown in FIG. 4, the walls defining envelope 220 are allowed to move away from each other, and therefore resilient element 215 within envelope 220 can expand from first thickness T1, as shown in FIG. 3, to a second thickness T2, as shown in FIG. 4, wherein T2 is greater than T1. Preferably, second thickness T2 is at least about twice first thickness T1. (Although the resilient member is often described as expanding from one thickness to another, the term thickness can also include directions other than the z-direction, including lateral or longitudinal expansion. Further, it should also be noted that the expansion of the resilient element may be in two or more directions, i.e. laterally and in the z-direction.)

The term "compressed" as applied to resilient element 215 means that element 215 has a reduced thickness, by virtue of the application thereto of a compressive force, as compared with its free, unrestrained thickness. The reduced thickness of resilient element 215 within sealed envelope 220 is preferably no more than about one half the free, unrestrained thickness of element 215. By "resilient" is meant that element 215 can be compressed (such as by a Z-direction compressive force) from its free, unrestrained initial thickness to a lesser thickness, and that upon release of the force operating to maintain element 215 in a compressed condition, element 215 will expand within about 10 to about 20 minutes to a thickness that is at least about 70 percent, and preferably at least about 90 percent, of its initial, free, unrestrained thickness.

Diaper 20 can also include a fastening system including, for example, a pair of fasteners 54, such as tape tabs or mechanical fasteners, that can be positioned in rear waist region 24 for connection with front waist region 22 to fasten diaper 20 in wearing position about the torso of a wearer. Alternatively, fasteners 54 can be positioned in the front waist region 22 or any other part of the diaper, if desired. Although the fastening system preferably comprises tape tabs and/or hook and loop fastening components, any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. Another exemplary fastening system is disclosed in co-pending U.S. application Ser. No. 09/143,184 filed Aug. 28, 1998 entitled "Absorbent Article Fastening Device", in the names of Kline et al. The fastening system may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; 5,591,152. Each of these patents is incorporated herein by reference. In alternative embodiments, opposing sides of the garment may be seamed or welded to form a pant. This allows the article to be used as a pull-on diaper or training pant.

Figure 6:
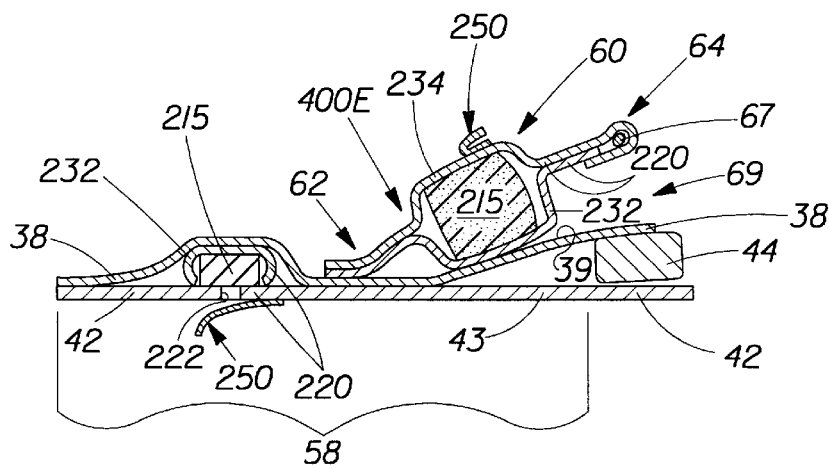
FIG. 6 is a fragmentary cross-sectional view taken along the line 6—6 of FIG. 2 showing expandable components disposed adjacent side margins of the diaper, including an expandable component disposed at a leg cuff of the diaper.

The diaper can also have a waist elastic feature, gasket cuffs, and barrier leg cuffs 60 (see FIGS. 2 and 6). Barrier leg cuffs 60 have a proximal edge 62 joined to a side margin area 58 of diaper 20, and have a distal edge 64 spaced outwardly from topsheet 38.

Leg cuffs can also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803, issued to Aziz et al. on Feb. 28, 1989, and Mar. 20, 1990, respectively, describe disposable diapers having "stand-up" elasticized flaps (barrier cuffs) which improve the containment of the leg regions. U.S. Pat. Nos. 4,695,278 and 4,795,454, issued to Lawson on Sep. 22, 1987, and to Dragoo on Jan. 3, 1989, respectively, describe disposable diapers having dual cuffs, including gasketing cuffs and barrier cuffs. The disclosures of each of those patents are hereby incorporated herein by reference to illustrate suitable gasket cuff structures and suitable barrier leg cuff structures. In some embodiments, it may be desirable to treat all or a portion of the leg cuffs with a lotion.

A suitable elasticized waistband structure for a disposable diaper can be constructed in a number of different configurations. Structures described in U.S. Pat. No. 4,515,595, which issued to Kievit et al. on May 7, 1985; U.S. Pat. No. 4,710,189, which issued to Lasch on Dec. 1, 1987; U.S. Pat. No. 5,151,092, which issued to Buell on Sep. 9, 1992; and U.S. Pat. No. 5,221,274, which issued to Buell on Jun. 22, 1993, can be employed. Other suitable waist configurations can include waistcap features such as those described in U.S. Pat. No. 5,026,364, which issued to Robertson on Jun. 25, 1991 and U.S. Pat. No. 4,816,025, which issued to Foreman on Mar. 28, 1989. The disclosures of each of the above-identified references are incorporated herein by reference to the same extent as if fully rewritten.

In one embodiment of the present invention, expandable component 200 can include a spacer 300 that can be disposed within diaper 20 between topsheet 38 and backsheet 42, as shown in FIGS. 1 through 4. Spacer 300 defines a fecal matter collection space 311 (see FIG. 4). In the embodiment shown in the drawings, spacer 300 is positioned between absorbent core 44 and backsheet 42. Preferably, however, spacer 300 is positioned between absorbent core 44 and topsheet 38, an embodiment that will be described hereinafter.

In another embodiment of the present invention, one or more expandable components can be provided in the form of waist area seals, such as seals 400A and 400B shown in FIG. 1. Seals 400A and 400B, when expanded, can serve to block leakage of body exudates from between the body of the wearer and front and rear waist regions 22 and 24, respectively. A waist seal can be placed in one or both waist regions, it or they can cover all or part of a waist region, and there can be more than one seal per waist region. And if more than one such seal is provided, the seals can be of the same or different resilient materials, and they can be activated by the same or different activators.

Additionally, expandable components can also be provided in the form of longitudinally-extending edge seals 400C and 400D which, when expanded can serve to block leakage of body exudates from between the body of the wearer and side margins 58. An edge seal can be placed in one or both edge regions, it or they can cover all or part of an edge region, and there can be more than one seal per edge region. And if more than one such seal is provided, the seals can be of the same or different resilient materials, and they can be activated by the same or different activators.

In yet another embodiment of the present invention, an expandable component can be provided in the form of longitudinally-extending leg cuff seals 400E that are disposed inwardly of and adjacent to barrier leg cuffs 60, as shown in phantom in plan view in FIG. 2, and as shown in cross section in FIG. 6. Leg cuff seals 400E, when expanded, can also serve to block leakage of body exudates between the body of the wearer and leg cuffs 60.

Referring again to FIG. 1, there is shown an embodiment of diaper 20 in which topsheet 38 and backsheet 42 have length and width dimensions that are generally larger than the corresponding dimensions of absorbent core 44. Thus, topsheet 38 and backsheet 42 each extend longitudinally beyond laterally extending core ends 45A and 45B to form front and rear waist regions 22 and 24. Topsheet 38 and backsheet 42 also extend laterally outwardly of core side edges 45C and 45D to define side margins 58. Although topsheet 38, backsheet 42, and absorbent core 44 can be assembled in a variety of well-known configurations, preferred diaper configurations are described generally in U.S. Pat. No. 3,860,003, which issued to Buell on Jan. 14, 1975, and in U.S. Pat. No. 5,151,092, which issued to Buell on Sep. 29, 1992, the disclosures of each of which patents are hereby incorporated herein by reference.

Spacer 300 shown in FIG. 1 can have a "keyhole" shape that is defined by a closed figure having an open inner area, wherein the open inner area is elongated and is wider at one end than it is at the other, opposite end. Suitable other closed shapes for spacer 300 include, but are not limited to, a circle, an oval, a rectangle, or another polygonal shape. Alternatively, spacer 300 can be provided in the form of an open-ended shape, such as the generally U-shaped form shown in FIG. 2 with the open end of the U facing rear waist portion 24.

Spacer 300 preferably includes a laterally extending portion 320 joining two longitudinally extending portions 322.

Suitable shapes and dimensions for a spacer 300 are disclosed in U.S. Pat. No. 5,330,459, entitled "Disposable Absorbent Article Having an Inflatable Spacer," which issued on Jul. 19, 1994, to LaVon et al.; U.S. patent application Ser. No. 08/081,733, filed Jun. 23, 1993 in name of Ahr et al.; U.S. patent application Ser. No. 07/898,047, filed Jun. 11, 1992 in name of Allen et al.; and U.S. Pat. No. 5,171,236, which issued on Dec. 15, 1992, to Dreier et al., the disclosures of each of which are hereby incorporated herein by reference. It is noted that a continuation of application Ser. No. 08/081,733 was filed as application Ser. No. 08/422,676 on Apr. 13, 1995 and matured into U.S. Pat. No. 6,180,847 issued on Jan. 30, 2001. It is also noted that a continuation of application Ser. No. 07/898,047 was filed as application Ser. No. 08/698,471 on Aug. 15, 1996 and matured into U.S. Pat. No. 6,168,584 issued on Jan. 2, 2001.

In embodiments where expandable component 200 serves to define a fecal matter collection volume, spacer 300, topsheet 38 and absorbent core 44 can include openings 46 and 47, respectively, as shown in FIG. 4, to provide access to collection space 311. Openings 46 and 47 can advantageously be in registry with one another, as shown in FIG. 4, to provide a passageway to allow fecal material to enter collection space 311.

As used herein, a "collection space" is a cavity between topsheet 38 and backsheet 42. The cavity is adapted to receive fecal material and preferably has a Z-direction height of at least about 0.65 centimeters (0.25 inch) and a volume of at least about 16.4 cubic centimeters (1.0 cubic inch). The effective volume of collection space 311 can be reduced if absorbent core 44 and resilient element 215 are compressed by the wearer's weight when the wearer is seated, for example. When resilient element 215 expands to second thickness T2, spacer 300 provides the desired volume of collection space 311 for receiving fecal matter.

Topsheet 38 and backsheet 42 are generally coextensive and are preferably at least partially peripherally joined together. As used herein the term "joined" refers to a condition where a first member or component is affixed or connected to a second member or component, either directly or indirectly, and it also refers to a condition where the first member or component is affixed or connected to an intermediate member or component that, in turn, is affixed or connected to the second member or component.

Topsheet 38 and backsheet 42 can be joined together by any means well known in art, such as adhesive bonding, heat sealing, ultrasonic bonding, or the like. Suitable adhesives for joining topsheet 38 and backsheet 42 include Century 5227 adhesive manufactured by Century Adhesives, Inc. of Columbus, Ohio; HL1258 adhesive sold by H. B. Fuller Company of St. Paul, Minn.; or Findley H2031 hot melt adhesive manufactured by Findley Adhesive Company of Elmgrove, Wis. The adhesive can be applied in any convenient form, such as beads, bands, or spirals.

As used herein, the term "absorbent core" refers to any component of diaper 20 used for absorbing and retaining body exudates. Absorbent core 44 can have opposed major faces and can, if desired, be encased within one or more layers of tissue (not shown). Additionally, absorbent core 44 can be made from a variety of commonly used materials, such as comminuted wood pulp, typically referred to as airfelt. If desired, absorbent core 44 can also contain absorbent gelling materials, as are commonly used in the art. In particular, absorbent core 44 can be made in accordance with the teachings of U.S. Pat. No. 4,610,678, which issued on Sep. 9, 1986, to Weisman et al.; U.S. Pat. No. 4,673,402, which issued on Jun. 16, 1987, to Weisman et al.; U.S. Pat. No. 4,834,735, which issued on May 30, 1989, to Alemany et al.; U.S. Pat. No. 5,147,345, which issued on Sep. 15, 1992, to Young et al.; U.S. Pat. No. 5,217,445, which issued on Jun. 8, 1993, to Cook et al.; and U.S. Pat. No. 5,234,423, which issued on Aug. 10, 1993, to Alemany et al., the disclosures of which patents are hereby incorporated herein by reference to show how to make an absorbent core 44 that is suitable for use with the present invention. In that regard, absorbent gelling materials made in accordance with commonly assigned U.S. Pat. No. Re. 32,649, entitled "Hydrogel-Forming Polymer Compositions for Use in Absorbent Structures," which issued on Apr. 19, 1988, to Brandt et al., are also suitable for use in a diaper 20 in accordance with the present invention.

Absorbent core 44 can be joined to the underside of topsheet 38, as shown in FIG. 3. Alternatively, core 44 can be joined to backsheet 42, or core 44 can include two or more layers. Core 44 can be adhesively joined to topsheet 38 or to backsheet 42 by any attachment means known in the art. Suitable attachment means include, but are not limited to, beads of adhesive and longitudinal and transverse bands or spirals of adhesive. Suitable adhesives for joining core 44 to other components of diaper 20 include XPO-9-035 adhesive, manufactured by Minnesota Mining and Manufacturing Company of St. Paul, Minn., as well as the Century 5227, Fuller HL1258, and Findley H2031 adhesives referred to hereinabove.

Referring again to FIG. 1, the term "topsheet" refers to any liquid-pervious facing of diaper 20 that is intended to contact the skin of a wearer while diaper 20 is worn and that prevents substantial contact of absorbent core 44 with the skin of the wearer. Additionally, topsheet 38 is preferably compliant, tactilely pleasing, and non-irritating to the skin of a wearer. Topsheet 38 can be treated to be hydrophilic, in order more readily to transport fluid exudates to absorbent core 44.

A suitable topsheet 38 can be made from materials such as porous foams, apertured plastic films, natural fibers (e.g., wood fibers or cotton fibers), synthetic fibers (e.g., polyester, or polypropylene fibers), or combinations thereof. A particularly preferred topsheet 38 includes polypropylene fibers having a denier of about 2.2 and a length of about 15.9 millimeters (0.62 inches). Topsheet 38 can be manufactured according to a number of known techniques. For example, topsheet 38 can be a nonwoven web defined by fibers that are spunbonded, carded, wet-laid, meltblown, hydroentangled, of combinations thereof. A suitable topsheet 38 is one that is carded and thermally bonded, has a basis weight of about 18 to about 25 grams per square meter, and is available from Veratec, Inc., Division of International Paper Company, of Walpole, Mass. under the designation P-8.

In addition to the desirable quality of softness that a topsheet made from a nonwoven material provides, such a topsheet can also be made to be elastically extensible. Extensibility is desirable because it provides improved fit of the diaper. Fully or partially elastically extensible topsheets are disclosed in U.S. Pat. No. 4,892,536, entitled "Absorbent Article Having elastic Strands," which issued on Jan. 9, 1990, to DesMaris et al.; U.S. Pat. No. 4,990,147, entitled "Absorbent article with elastic Liner for Waste Material Isolation," which issued on Feb. 5, 1991, to Freeland; and U.S. Pat. No. 5,269,775, entitled "Trisection Topsheets for Disposable Absorbent Articles and Disposable Absorbent Articles Having such Trisection Topsheets," which issued on Dec. 14, 1993, to Freeland et al., the disclosures of each of which patents are hereby incorporated herein by reference.

Openings 46 and 47 can be laterally centered on longitudinal axis 36. Opening 46 can be of any suitable shape, such as an oval having a longitudinal dimension, in one embodiment, of at least about 5.1 centimeters (2.0 inches) and a transverse dimension of at least about 3.8 centimeters (1.5 inches). The rearwardmost edge of aperture 46 can be disposed at least about 15.2 centimeters (6.0 inches) from rear edge 32B of diaper 20 while it is worn. In one embodiment the rearwardmost edge of aperture 46 is between about 17.8 centimeters (7.0 inches) and about 21.6 centimeters (8.5 inches) from rear edge 32B of diaper 20 while it is worn. As will be appreciated by those skilled in the art, the is location and size of opening 46 can be varied to accommodate different size wearers.

Opening 47 is preferably in registry with opening 46, and it can have a shape the same as, or similar to, the shape of opening 46, if desired. Preferably, spacer 300 is in registry with each of openings 46 and 47 such that spacer 300 does not substantially obstruct opening 46 or opening 47, and such that at least a portion of each of openings 46 and 47 is disposed between longitudinally extending portions 322 of spacer 300. If desired, spacer 300 can be joined to body facing surface 39 of topsheet 38.

Backsheet 42 is preferably impervious to fluids, such as urine, and prevents fluids absorbed by and contained in absorbent core 44 from wetting undergarments, clothing, and bedding. As used herein, the term "backsheet" refers to any barrier disposed outwardly of absorbent core 44 as diaper 20 is worn, and that retains absorbed liquids within diaper 20. Backsheet 42 is preferably a thin thermoplastic film, although other flexible, preferably liquid-impervious materials can also be used. As used herein, the term "flexible" refers to materials that are compliant and that will readily conform to the general shape and contours of the human body.

Backsheet 42 can include a woven or nonwoven material, polymeric films such as thermoplastic films of polyethylene or polypropylene, or composite materials such as film-coated nonwoven material. Backsheet 42 can be a thermoplastic film having a thickness of from about 0.01 mm to about 0.051 mm (0.0004 to 0.002 inches). If desired, backsheet 42 can be embossed or matte finished to provide a cloth-like appearance. A suitable material from which backsheet 42 can be formed is a polyethylene film having a thickness of from about 0.010 mm to about 0.051 mm. Suitable polyethylene films are manufactured by Clopay Corp., of Cincinnati, Ohio, under the designation P-18-1401, and by Tredegar Industries, of Terre Haute, Ind., under the designations X8297 and HTS-5, FSII. Other suitable materials from which backsheet 42 can be formed include RR8220 blown films and RR5475 cast films manufactured by Tredegar Industries.

One or both of topsheet 38 and backsheet 42 can be extensible, and can be formed from an elastomeric or a stretchable film. Extensible components are described in International Patent Publication No. WO 93/01785, entitled "Stretchable Absorbent Articles," which was published on Feb. 4, 1993, the disclosure of which is hereby incorporated herein by reference. For example, backsheet 42, or portions thereof, can include a structural, elastic-like film (SELF) web. A structural, elastic-like film web is an extensible material that exhibits an elastic-like behavior in the direction of elongation without the use of added elastic materials.

One example of a SELF web suitable for the present invention is more completely described in commonly assigned U.S. Pat. No. 5,518,801 entitled Web Materials Exhibiting Elastic-Like Behavior, which issued to Chappell, et, al. on May 21, 1996, the disclosure of which is hereby incorporated herein by reference.

Referring to FIGS. 3 and 4, expandable component 200 includes a substantially gas impermeable envelope 220 that encloses resilient element 215. Envelope 220 can be formed by positioning resilient element 215 between two flexible envelope walls 232 and 234, compressing resilient element 215 between walls 232 and 234, and joining and sealing the marginal edges of walls 232 and 234 to form a cavity 236 therebetween within which resilient element 215 is retained in compressed form. Suitable materials from which walls 232 and 234 can be formed include thermoplastic films, metallic foils, and laminates thereof. For example, a suitable film is a polyethylene film having a thickness of from about 0.010 mm to about 0.051 mm. Suitable polyethylene films are manufactured by Clopay Corp., of Cincinnati, Ohio, under the designation P-18-1401, and by Tredegar Industries, of Terre Haute, Ind., under the designations X8297 and HTS-5, FSII. Other suitable materials from which walls 232 and 234 can be formed include RR8220 blown films and RR5475 cast films manufactured by Tredegar Industries, and a polyethylene film available from Tredegar Industries and designated C-8323. Preferred materials for walls 232 and 234 include a 3.0 mil Nylon/LDPE/Surlyn coextruded film, which is available as product C735H-014 from Printpack, Inc., of Atlanta, Ga., and a 3.0 mil Nylon/LLDPE coextruded film available as products C733H-010 and C733-010 from Printpack, Inc.

Flexible walls 232 and 234 can be formed from two separate pieces of material. Alternatively, they can be formed from a single piece of folded-over material, or a continuous tube formed from a single material. As shown in FIGS. 3 and 4, a portion of envelope 220 can be defined by backsheet 42 in that wall portion 234 of envelope 220 is an integral part of backsheet 42, and in that marginal edge portions of wall portion 232 are joined directly to the inwardly-facing surface of backsheet 42. Alternatively, wall portion 234 can be formed from a piece of material that is separate from backsheet 42, and envelope 220 can be joined directly to backsheet 42 by fastening wall portion 234 thereof to the inwardly-facing surface of backsheet 42, such as by the use of an adhesive, or the like.

With resilient element 215 positioned between walls 232 and 234, walls 232 and 234 can be pressed together by a compressive force to compress element 215. While element 215 is compressed, walls 232 and 234 can be joined to define marginal seams by any suitable joining method, such as heat/pressure sealing, adhesive bonding, ultrasonic bonding, or the like, to completely seal together portions of walls 232 and 234 that surround element 215, to prevent the inflow of air to cavity 236 upon the release of the compressive force after sealing has been effected. Suitable seams can be formed by using Findley H2031 hot melt adhesive to join the edge of wall 232 to wall 234 that is part of backsheet 42. In one embodiment, air between walls 232 and 234 can be evacuated as walls 232 and 234 are joined together, such as with vacuum sealing equipment known in the art, so that sealed envelope 220 remains in substantially flattened condition with resilient element 215 in compressed form.

In one embodiment of the present invention one or both of walls 232 and 234 can be formed from an elastomeric or stretchable film, so that the walls are extensible and can accommodate expansion of resilient element 215 once envelope 220 is opened to the ambient atmosphere. For instance, one or both of walls 232 and 234 can be a SELF web described in commonly assigned U.S. Pat. No. 5,518,801 entitled Web Materials Exhibiting Elastic-Like Behavior, which issued to Chappell, et, al. on May 21, 1996, the disclosure of which was earlier incorporated herein by reference. Alternatively, one or both of walls 232 and 234 can be pre-formed, such as by vacuum forming, embossing, or folding, to accommodate expansion of resilient element 215. For instance, one or both of walls 232 and 234 can have pleats for accommodating expansion of resilient element 215. In FIG. 3 wall 232 is shown having longitudinally extending pleats 235. In yet another embodiment, walls 232 and 234 can accommodate expansion of resilient element 215 if unbonded portions of each of walls 232 and 234 bounding cavity 236 are sized to have a larger projected area than that of resilient element 215, as described below.

Figure 21:
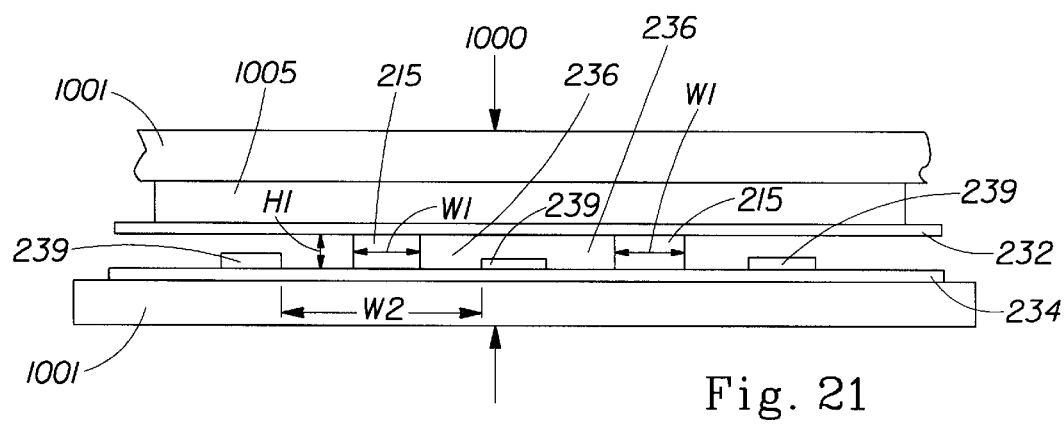
FIG. 21 is a schematic illustration of a method and apparatus for forming an expandable-component-containing envelope in accordance with the present invention.

FIG. 21 is a schematic illustration of one form of apparatus for providing an expandable component 200. Walls 232, 234 and resilient element 215 are shown positioned between two spaced, substantially parallel plates 1001, formed from Plexiglas, or the like. Resilient element 215 has an initial width W1, and a free, unrestrained initial thickness H1 before it is compressed between walls 232 and 234. Portions of an adhesive 20 layer 239 are spaced from each other on a surface of wall 234 so that portions of walls 232 and 234 therebetween remain unbonded. Spacing W2 between the several portions of adhesive layer 239 can be selected so that the unbonded portions of walls 232 and 234 bounding cavity 236 have a larger area than that of resilient element 215. Walls 232 and 234 can thereby accommodate subsequent expansion of resilient element 215. For instance, spacing W2 can be selected to be greater than or equal to the sum of W1 and H1 to accommodate expansion of resilient element 215 to a thickness of about H1 upon the opening of envelope 220. Alternatively, spacing W2 can be made smaller to restrict expansion of resilient element 215 upon exposing an opening in envelope 220.

A compressive load 1000 is applied to plates 1001 to move walls 232 and 234 together. A conformable piece 1005 can be positioned between one of plates 1001 and wall 232. Conformable piece 1005 aids in distributing compressive load 1000 over the surface of wall 232, pressing the air from within resilient element 215 and from between walls 232 and 234, and reducing the wrinkling of wall 232 as wall 232 is adhesively joined to wall 234. The stiffness of conformable piece 1005 in compression should be less than or about equal to the stiffness of resilient element 215 in compression. Conformable piece 1005 can be formed from the same material as that from which resilient element 215 is formed, and it can have a thickness greater than or equal to thickness H1 of resilient element 215.

Figure 5:
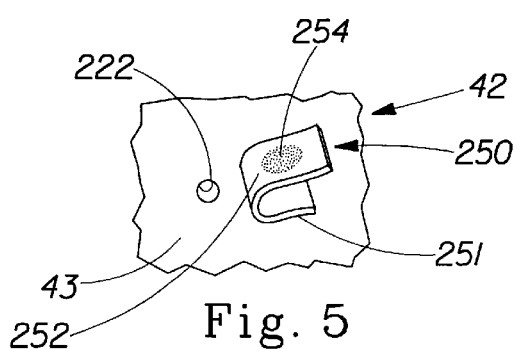
FIG. 5 is an enlarged, fragmentary perspective view of a portion of an air impermeable envelope containing an expandable component, and including a releasable closure for covering an access aperture.

Referring to FIG. 5, a wall of gas impermeable envelope 220 can include an aperture 222 that is provided in one of walls 232 or 234, to allow ambient air to enter the envelope. A releasable closure flap 250 to cover aperture 222 can include a piece of film 251 that is joined to the outer surface of the wall through which aperture 222 extends, and adjacent to the aperture. If desired, closure flap 250 can be made from the same material as that from which walls 232 and 234 are made, and it can be joined to the outer surface of envelope 220 by any suitable method, including, but not limited to, adhesive bonding, mechanical bonding, ultrasonic bonding, heat sealing, and the like. Closure flap 250 can be partially or completely manually peeled relative to the surface of envelope 220 to expose and to open aperture 222, thereby permitting air to enter cavity 236 to enable expansion of resilient element 215 to take place within cavity 236. The area of aperture 222 can be selected to provide a desired rate at which resilient element 215 expands once releasable closure flap 250 is peeled from over aperture 222. Thus, resilient element 215 will expand more rapidly as the area of aperture 222 is increased. Other structures are also contemplated to increase or decrease the rate of airflow through the aperture 222, such as covering all or a portion of the aperture with a breathable film or other material which allows air to pass at a certain rate.

Film 251 can carry an adhesive 252 for adhering film 251 to the surface of the wall through which aperture 222 extends. Suitable pressure sensitive adhesives for use with closure flap 250 include Century Adhesive A-305-IV, manufactured by Century Adhesives Corporation, of Columbus, Ohio; Adhesive Number 34-2823, manufactured by National Starch and Chemical Company, of Bridgewater, N.J.; and Fuller Adhesive numbers HL-2238-XZP and HL-2254-XZP, manufactured by H. B. Fuller Company, of Vadnais Heights, Minn.

In an alternative embodiment for joining closure flap 250 to the envelope wall, a first material can surround aperture 222, and closure flap 250 can include on an envelope-facing surface thereof a second material that is cohesive with the first material. In another embodiment, closure flap 250 can be in the form of a piece of pressure-sensitive tape, such as Scotch Brand Model 600 transparent tape, manufactured by 3M Company, of Minneapolis, Minn.

In another alternative embodiment, envelope 220 can be formed without a pre-formed aperture 222. Instead, closure flap 250 can include a relatively low tack adhesive area 252 to releasably retain closure 250 in the desired position, and a relatively high tack adhesive area 254 adjacent low tack adhesive area 252, as shown in FIG. 5. Closure 250 can be easily peeled from the surface of envelope 220 at the low tack adhesive area, while continued peeling causes high tack adhesive 254 to tear the wall of envelope 220, thereby creating an opening in envelope 220 through which air can enter.

In yet another embodiment, both aperture 222 and closure flap 250 can be omitted, and air-impermeable envelope 220 can be opened by manually tearing walls 232 and 234 apart, or by cutting a surface of envelope 220 with a pair of scissors, by piercing envelope 220 with a lancet or the like.

Resilient element 215 is preferably made from a porous material so that when it is in a compressed condition and an opening is formed in envelope 220, the admission of ambient air into envelope 220 allows resilient element 215 to decompress and to expand to an increased thickness. In one such embodiment, resilient element 215 can be provided in the form of a porous, sponge-like structure, such as an open-celled foam, which can be an open-celled polymeric foam. An open-celled foam is generally characterized in that it includes a multiplicity of relatively small, individual cells that are for the most part not completely isolated from each by the walls of adjacent cells, but that are instead substantially interconnected with each other. Open celled foams, as used herein, can include foams that are initially closed celled, and that are reticulated, such as by compression, to form an open celled structure within envelope 220. One suitable foam from which resilient element 215 can be made is a polyurethane foam that is available as #1230 foam from American Excelsior Corp. of Cincinnati, Ohio. Another suitable porous, open celled foam is a foam prepared by polymerizing a high internal phase emulsion, such as is described in U.S. Pat. No. 5,147,345, entitled "High Efficiency Absorbent Articles for Incontinence Management," which issued on Sep. 15, 1992, to Young et al., the disclosure of which is hereby incorporated herein by reference.

The pore volume of resilient element 215 can be at least about 2 ml/gram, and in one embodiment is between about 2 to about 100 ml/gram prior to compression in envelope 220, as measured in the above-identified U.S. Pat. No. 5,147,345. Pore volume is a measure of the volume in a porous foam structure of open cells per unit mass of solid material that forms the foam structure. Pore volume influences flexibility, compressibility, and deflection characteristics of resilient element 215. For a given material, as pore volume increases, flexibility increases and resistance to compression generally decreases. In addition, as pore volume increases, the quantity of air per unit weight of resilient element 215 that can be drawn into envelope 220 as resilient element 215 expands also increases. Accordingly, increased Z-direction thickness can be obtained with a relatively small amount and weight of material.

Resilient element 215 can have a cell size of at least about 5 microns prior to compression within envelope 220, in accordance with the measurement technique disclosed in above-identified U.S. Pat. No. 5,147,345. For a given material, the rate at which resilient element 215 expands will generally increase as the cell size increases.

Resilient element 215 can have a density prior to compression within envelope 220 of less than about 1.0 gram per cubic centimeter, and in one embodiment it has a density between about 0.01 to about 0.50 grams per cubic centimeter, as measured in accordance with the method disclosed in U.S. Pat. No. 5,147,345. The density of resilient element 215 also influences the flexibility, the compressibility, and the deflection characteristics of the resilient element. In general, for a given material, as the density decreases the flexibility increases and the resistance to compression decreases.

By way of example, a spacer 300 was formed using layers of a porous, open celled foam having a density of about 0.03 gm/cc, a pore volume of about 32 ml/gram, and a cell size of between about 50 and about 75 microns. The foam can be made according to the teachings of above-identified U.S. Pat. No. 5,147,345, using a monomer composition similar to that provided in Example 6 of that patent.

Resilient element 215 included seven layers of porous open celled foam, each layer having a closed shape enclosing an open area, and each layer having a shape generally the same as the shape of the other layers. Each layer had a width W1 (see FIG. 21) of about 12.7 mm (0.5 inch) as measured around the perimeter of the closed shape, and a surface area of about 30 square centimeters, with each layer enclosing an open area of about 30 square centimeters. Each layer of foam had a free, unrestrained thickness of about 0.070 inch, so that resilient element 215 had a total Z-direction thickness H1 of about 0.49 inch before compression.

Findley H2301 adhesive was applied to one side of a first sheet of polyethylene, the sheet of polyethylene having a thickness of about 0.0010 inch (0.025 mm). Adhesive was applied to the sheet of polyethylene so as to leave an adhesive-free area having a closed shape. The adhesive-free area was sized to have a projected area larger than that of layers forming resilient element 215, to thereby accommodate expansion of resilient element 215. Width W2 FIG. 21) of the adhesive-free area at any point around the perimeter of the adhesive-free area was about 2.54 centimeters (1.0 inch), or about equal to height H1 plus width W1.

An aperture 222 having a diameter of about 0.5 inch was cut in a first sheet of polyethylene, and was covered with a piece of Scotch Brand Model 600 transparent tape on the side of the first sheet of polyethylene to which adhesive was not applied. Seven layers of foam were then placed between the first sheet of polyethylene and a second sheet of polyethylene. The seven layers of foam were then compressed by pressing the two sheets of polyethylene and seven layers of foam together between two plates of Plexiglas methyl methacrylate, in the manner shown generally in FIG. 11. The compressive loading was about 28 psi. While maintaining that compressive loading, the edges of the first and second sheets of polyethylene were pressed together to adhesively join the sheets around the perimeter of the spacer to provide an air impermeable envelope 220.

The total caliper of the spacer, including the thickness of both sheets of polyethylene and the seven layers of compressed foam, was about 0.150 inch. A piece of transparent tape was then removed from aperture 222, and the Z-direction caliper of the spacer was measured at predetermined time intervals. Z-direction caliper was measured using a dial indicator, and was measured under a confining pressure of about 0.24 psi with confining pressure applied to the spacer with a load foot having a 1.0 square inch surface area. The spacer had the Z-direction calipers shown in Table I below for the indicated times after removing the tape from the aperture in the first polyethylene sheet.

TABLE I

| TIME - SECONDS | CALIPER - INCHES |
| --- | --- |
| 0 | 0.150 |
| 5 | 0.175 |
| 10 | 0.190 |
| 30 | 0.255 |
| 45 | 0.290 |
| 120 | 0.402 |
| 300 | 0.460 |

Referring to FIGS. 1 through 4 and FIG. 6, expandable component 200 can also be in the form of an elongated seal 400 for reducing leakage of body exudates from between the absorbent article and the wearer's skin, or for increasing the comfort of the wearer. Such seals 400 can include waist region seals 400A and 400B, positioned within front and rear waist regions 22 and 24, respectively, and also side margin seals 400C and 400D, positioned within side margins 58. Each of seals 400 can include a compressed, resilient element 215 disposed within an air impermeable envelope 220. Waist region seals 400A, 400B can each have a generally laterally extending, elongated resilient element 215, and side margin seals 400C, 400D can each have a generally longitudinally extending, elongated resilient element 215. Resilient elements 215 can be disposed between top sheet 38 and backsheet 42, as shown in FIGS. 3 and 4. Further, a single seal can encircle the entire perimeter of the article, or multiple seals can be placed along a portion of or along the entire perimeter.

Referring to FIGS. 3, 4, and 6, seals 400 expand from a first thickness T1 (see FIG. 3) to a second thickness T2 (see FIG. 4) that is greater than first thickness T1. Expansion occurs upon the opening to the ambient atmosphere of envelope 220 enclosing resilient element 215.

Referring to FIGS. 2 and 6, diaper 20 can also include side margin seals 400E, wherein each side margin seal 400E is associated with a barrier leg cuff 60. Each barrier leg cuff 60 extends generally longitudinally along a side margin 58 of diaper 20 and has proximal edge 62 joined to an underlying portion of diaper 20 in side margin 58, and distal edge 64 spaced from proximal edge 62. Distal edge 64 can include a spacing element 67, such as an elastic element, for spacing distal edge 64 from body facing surface 39 of topsheet 38. The elastic element and the seal 400E can be adjacent each other or they can at least partially coincide in lateral and/or longitudinal locations relative to the centerlines of the article.

Barrier cuff 60 includes a resilient element 215 disposed within an air impermeable envelope 220. Air impermeable envelope 220 can include a first flexible wall 232 and a second flexible wall 234, and each of walls 232 and 234 can be formed from a polymeric film, such as a polyethylene film. Walls 232 and 234 can be joined together along the lengths of proximal and distal edges 62 and 64, as well as at the ends of the barrier leg cuffs positioned in front and rear waist regions 22 and 24. In the embodiment shown in FIG. 6, wall 232 is joined to topsheet 38 at proximal edge 62. Wall 232 can be joined to topsheet 38 by any suitable means, including, but not limited to, adhesive, ultra-sonic, mechanical, or heat bonding. Wall 234 is folded to form a hem for containing spacing element 67, and is joined to wall 232 along distal edge 64.

Wall 234 can include an aperture 222 covered by a closure flap 250. Upon the opening of closure flap 250, resilient element 215 expands from an initial compressed condition. Expansion of resilient element 215 provides a seal between diaper 20 and the wearer's skin and also helps to space distal edge 64 from topsheet 38, and thereby forms a channel 69 intermediate barrier leg cuff 60 and topsheet 38. Channel 69 holds liquid and solid body exudates that could otherwise leak from between side margin 58 and the wearer's skin.

FIG. 6 shows a barrier cuff 60 having both a spacing element 67 and an expandable seal 400E. Alternatively, spacing element 67 could be omitted, if desired. In embodiments where spacing element 67 is omitted, seal 400E can be positioned at distal edge 64 of barrier cuff 60. Additionally, the elastic element and the seal 400E can be adjacent each other or they can at least partially coincide in lateral and/or longitudinal locations relative to the centerlines of the article.

In a still further embodiment of the present invention, the garment, in the form of a disposable diaper 20a, can have the structure shown in longitudinal cross section in FIG. 7. In that embodiment envelope 220, which encloses and contains compressed resilient element 215, can be opened by a user without the need for the user to directly grip and to peel a closure flap from the envelope or from the garment, and without the use of a cutting or puncturing implement for directly manually cutting or puncturing the envelope. In that regard, the formation of an opening in the envelope wall is effected by a user's application of tension to the garment before applying the garment to the body of the wearer. The application of tension causes an activator that is connected both with the envelope and also with the garment to provide an opening in the envelope.

In the embodiment shown in FIG. 7, envelope 220 is positioned between topsheet 38 and absorbent core 44 of diaper 20a, instead of between the absorbent core and the backsheet as in the embodiment shown in FIGS. 1 through 4. Included within diaper 20a is an optional intermediate sheet in the form of a secondary topsheet 43 that is positioned between topsheet 38 and absorbent core 44. Secondary topsheet 43 overlies the body-facing surface of absorbent core 44 and is liquid pervious, to allow urine and fluid, or relatively low viscosity, fecal matter to pass therethrough and to and into absorbent core 44 for collection and retention. In that connection, a suitable secondary topsheet material is a nonwoven sheet, such as the secondary topsheet described in U.S. Pat. No. 5,342,338, entitled "Disposable Absorbent Article for Low-Viscosity Material," which issued on Aug. 30, 1994, to Roe, the disclosure of which is hereby incorporated herein by reference. Additionally, secondary topsheet is preferably elastic, or it can be made from a material that is not intrinsically elastic and that is processed to have elastic properties, such as by the SELF process disclosed earlier herein. Additionally, if desired, secondary topsheet 43 can be of the same materials and of the same structure as the materials and structures hereinbefore identified in connection with topsheet 38.

Envelope 220 can be secured to topsheet 38 by adhesive layer 500. In that connection, adhesive layer 500 can define a connection or first retention point between envelope 220 and a substrate, which in this instance is topsheet 38, and it can be a continuous layer of adhesive that serves to secure the entire upper, body-facing surface of envelope 220 to topsheet 38, or, alternatively, adhesive layer 500 can be in the form of several smaller, spaced areas of adhesive, or a single smaller area of adhesive, as shown in FIG. 7. However, the envelope may also be retained in position by a retention point or points which acts by friction or may be held by other retention means such as a pocket, walls or barriers that block the movement of the envelope or by joining the envelope between two or more elements which prevent or reduce movement of the envelope within the article.

Further, envelope 220 can include one or more preformed opening 222 on a surface of the envelope that faces secondary topsheet 43, which, if desired, can be extensible in at least the longitudinal direction of the diaper. A mechanical activator 502 in the form of an elongated strip, rod, or the like preferably extends from envelope 220 to the inner surface of secondary topsheet 43 to a second retention point. As illustrated and described herein, activator 502 is formed from a substantially inextensible material, or from a material having an extensibility that is significantly lower than the extensibility either of secondary topsheet 43 or of backsheet 42.

Activator 502 is connected at one end 504 thereof with secondary topsheet 43 by a suitable second retention point, such as by adhesive layer 506, or by heat or ultrasonic sealing, friction or the like, so that end 504 of activator 502 is firmly and securely held by secondary topsheet 43. The opposite end 508 of activator 502 is connected with envelope 220 by a releasable connection arrangement, such as by a pressure-sensitive adhesive layer 510, or the like. Additionally, end 508 of activator 502 has a sufficiently large area to define a cover portion that completely overlies and surrounds aperture 222 provided in envelope 220. As shown, activator 502 can be connected with envelope 220 in such a manner that actuator 502 is partially doubled back upon itself at end 508, so that pulling on activator 502 in an outward direction, away from envelope 220, causes actuator end 508 to peel away from the surface of envelope 220, beginning at a point laterally inwardly of aperture 222 and proceeding in an outward direction. In that regard, the resistance to peeling of adhesive layer 510 is desirably relatively low, so that only a relatively low tensile force will be needed to peel activator end 508 from envelope 220.

Activation of resilient element 215 in the embodiment shown in FIG. 7 is accomplished by applying tension to the garment in at least one of the directions indicated by arrows T. The application of tension to the garment results in relative movement between the first retention point of envelope 220 and the diaper structure, defined in FIG. 7 by adhesive layer or spot 500, and the second retention point of activator 502 and secondary topsheet 43, defined in FIG. 7 by an adhesive layer or spot 506. That relative movement between the two spaced retention points results in their movement in opposite directions, so that retention points 500 and 506 move away from each other.

The ability of the retention points to be movable relative to each other can be provided by imparting to at least a portion of the garment structure an ability to be geometrically enlarged, such as by forming pleats, gathers, or the like in at least one element of the garment structure. Additionally, relative movement of the retention points can also be enabled by forming at least one of the structural elements of the garment structure from an extensible material, one that is either elastically extensible or one that is inelastically extensible. For example, one of topsheet 38, backsheet 42, or secondary topsheet 43 can be made to be extensible, and when a tensile force T is applied to the garment the relative inextensibility of activator 502 and of envelope 220 results in the activator moving laterally outwardly away from envelope 220, thereby peeling doubled-over activator end 508 from envelope 220, as shown in FIG. 8, and uncovering aperture 222. When aperture 222 is opened air can enter into envelope 220 to enable resilient element 215 to resiliently expand and to return to its substantially uncompressed condition. As a result of the decompression and enlargement of resilient element 215, a fecal matter collection space 311 is formed that serves to collect fecal matter and to minimize the contact area of the fecal matter with the skin of the wearer of the diaper.

Although shown as positioned on a surface of envelope 220 that faces backsheet 42, opening 222 in envelope 220 can also be positioned on a surface of envelope 220 that faces topsheet 38, if desired. In that arrangement, activator 502 would extend from the body-facing surface of envelope 220 to topsheet 38.

As discussed earlier herein, resilient element 215 is permitted to expand to its uncompressed condition, which can result in a resilient element thickness after decompression of somewhat less than the original, uncompressed thickness. And the resulting thickness after decompression is desirably reached at some time after uncovering of aperture 222, rather than immediately, so that the diaper can be properly positioned on the body of the wearer before full decompression of resilient element 215 occurs. And in the case of disposable diapers, which are generally worn as undergarments, it is desirable that full decompression occur some time after both the undergarment and the outer garments have all been applied to the wearer of the diaper.

The time from initial opening of aperture 222 to the time substantially full decompression of the resilient element 215 occurs can be increased by limiting the rate at which air is permitted to enter envelope 200 after aperture 222 has been opened. Because resilient element 215 can only expand within envelope 220 if outside air is allowed to enter the envelope and to enter and to fill the cells in the resilient element, limiting the rate of air flow into envelope 220 permits some degree of control over the rate of expansion of resilient element 215. One way to limit the rate of air flow into the envelope is to provide a pre-formed aperture that has a very small area. For example, for an aperture having an area of 0.03 mm$^2$ (equivalent to a circular aperture having a diameter is of 0.2 mm) the time for a compressed resilient element 215 to expand to about 90% of its maximum uncompressed thickness was found to be 18 seconds, whereas for an aperture having an area of 28.2 mm$^2$ (equivalent to a circular aperture having a diameter of 6.0 mm) the time for a compressed resilient element 215 to expand to about 90% of its maximum uncompressed thickness was found to be 90 seconds.

Another way to limit the rate of expansion of the resilient element is to provide a substantially open cell resilient element that has a low porosity outer skin that serves to delay decompression by slowing the rate at which ambient air can enter the interior cells of the resilient element.

A further way to limit the rate at which air enters envelope 220 and the cells of resilient element 215 is to place over aperture 222 a barrier that operates to slow air flow through aperture 222. The barrier can operate as a flow restriction to limit the rate of air flow into the envelope. One form of a such partial barrier is a gas-permeable film or a semipermeable membrane 512, as shown in FIGS. 9 and 10, which is positioned in overlying relationship with aperture 222. The barrier can include a microporous film, a monolithic film, foam, a nonwoven web, a woven web, adhesive or any combination of these or other suitable materials. Examples of suitable limited permeability membranes and films include those available from Clopay Corporation of Cincinnati, Ohio under the trade designations 201-1999 and BR 106. The relatively low permeability of membrane 512 operates to slow the rate at which air is permitted to enter envelope 220 through aperture 222.

In the embodiment shown in FIGS. 9 and 10, aperture 222 in envelope 220 is covered by a gas-permeable element, such as a thin, semipermeable membrane 512 or a gas-permeable film. The rate of expansion of resilient element 215 can be controlled by selecting a semi-permeable membrane or a gas-permeable film that has a gas diffusion coefficient that permits air to enter envelope 222 at a rate that provides a desired time for the expansion of the compressed resilient element to substantially 90% of its original, uncompressed thickness. Suitable gas-permeable membranes or films can have a permeability that can be measured by determining the moisture vapor transmission rate (MVTR) of the membrane or film. The MVTR of suitable membranes or films can be from about 500 gm H$_2$O/m$^2$/24 hr. to about 5000 gm H$_2$O/m$^2$/24 hr., as measured by the is test method described below. Films suitable for use as gas-permeable membrane 215 include films having the product designations 201-1999 and BR 106, which are available from the Clopay Corporation, of Cincinnati, Ohio.

The MVTR of a thin film can be measured by placing a quantity of a hydrophilic material, such as calcium chloride, into a non-porous, open-top vessel (not shown) having an outwardly-extending flange around the vessel opening. A portion of the material for which the MVTR is to be determined is placed in overlying relationship relative to the vessel opening and is in firm contact with the entire flange of the vessel so that the material under test completely covers the open end of the vessel. An annular gasket and an annular retaining ring are then placed over the sheet material and are securely clamped to the vessel flange by any convenient clamping arrangement, to tightly and completely seal the periphery of the vessel opening in order that air or moisture vapor can only pass through the material under test. The resulting assembly is then weighed to determine the initial weight of the vessel and its contents.

After the initial weight has been determined, the assembly is placed in a chamber having a constant temperature (40° C.) and a constant humidity (75% relative humidity). The vessel is maintained under those atmospheric conditions for a period of five (5) hours, after which it is removed from the chamber, wrapped tightly with an impervious film to prevent transfer of moisture into and out of the vessel, and is allowed to reach thermal equilibrium with the ambient atmosphere in which the weigh balance is located. Thermal equilibrium is generally achieved in about 30 minutes, after which the film overwrap is removed from the vessel. The vessel is then weighed to determine the final weight of the vessel as well as its contents.

The MVTR is calculated by the following formula, which provides the MVTR in gm $H_2O/m^2/24$ hr:

$$MVTR = \frac{(FinalWt\ (gm) - InitialWt\ (gm)) \times 24.0}{Sample\ Area\ (sq.\ meters) \times 5.0\ hr.}$$

As noted above, the rate of expansion of resilient element 215 can be controlled by changing the area of aperture 222 provided in envelope 220, or by covering aperture 222 with a gas permeable film or membrane 512 having the desired gas permeability. In general, decreasing the area of aperture 222, or decreasing the gas diffusion coefficient of a gas-permeable film or membrane 512 that covers aperture 222, will lengthen the time period within which resilient element 215 will reach a substantially fully decompressed condition. Conversely, increasing the area of aperture 222, or increasing the gas diffusion coefficient of a gas-permeable film or membrane 512 that covers aperture 222, will shorten the time period within which resilient element 215 will reach a substantially fully decompressed condition. Further, both the area of aperture 222 and the gas permeability of membrane or film 512 can be changed, if desired.

The ability to control the rate at which resilient element 215 expands provides a significant benefit to the user. In that regard, in some embodiments, if resilient element 215 expands too rapidly the product might achieve an increased bulk too soon and could render more difficult the application of outer clothing over the garment that includes the expanded element. If resilient element 215 expands too slowly, however, it may fail to perform its intended function in a timely manner. For example, if resilient element 215 is a spacer in a disposable diaper and is intended to define a collection chamber for feces, too slow an expansion rate could render the product fully functional at a time after defecation occurs. It is therefore preferred that in certain embodiments, the diaper be so configured as to permit the expansion of resilient element 215 sufficiently quickly to be available to perform its intended collection function, but slowly enough to allow easy application of the diaper and any outer clothing. In that connection, resilient element 215 preferably expands to about 90% of its original thickness in less than about 20 minutes from the time at which activation of expansion is initiated by providing an opening in envelope 220. In certain embodiments, it is also preferred that full expansion of resilient element 215 occurs not earlier than about 5 minutes from the time of initiation of activation. More preferably, expansion of resilient element 215 to about 90% of its original thickness occurs within about 6 minutes to about 15 minutes after activation is initiated by providing an opening in envelope 220. In other embodiments, the desired expansion time may shorter, for example, less than 5 minutes, less than 1 minute, less than 30 seconds or even less than 5 seconds.

In one suitable embodiment of the invention aperture 222 includes two spaced, 12 mm diameter openings, to provide a total open area of 226 $mm^2$. The openings can be covered by the above-identified gas-permeable Clopay Corporation 201-1999 film. Such a construction has been found to allow expansion to about 90% of the original, uncompressed thickness of the resilient element in about 6 minutes. Reducing the size of aperture 222 to a single 12 mm diameter opening, to provide an open area of 113 $mm^2$, was found to approximately triple the time required for the resilient element to expand to 90% of its original, uncompressed thickness.

The gas-permeable cover membrane or film can be secured in position over aperture 222 by any known bonding means including, but not limited to, adhesive bonding, mechanical bonding, ultrasonic bonding, thermal bonding, or any combination of those or any other suitable bonding means. In one preferred embodiment the gas-permeable membrane or film is secured in position over aperture 222 by bonding it to envelope 220 around the entire periphery of aperture 222.

The rate of expansion of the gas-permeable cover component that overlies aperture 222 can be closely controlled by varying both the aperture area and the permeability of the gas-permeable cover, as measured by the MVTR of that component. The table below shows the expansion rate, as measured by the time required for the resilient element to expand to 90% of its original, uncompressed thickness, for several combinations of aperture size, permeability of the gas-permeable aperture-cover, and the relative compressive resistance or stiffness of the resilient element. The resilient elements in the examples are open-celled, microporous, absorbent foams that were produced in accordance with the teachings of the aforementioned U.S. Pat. No. 5,147,345. The "soft" variant of the foam is one that undergoes compression of about 41% under a 1.0 psi applied pressure (i.e., the foam has a thickness under that pressure equal to about 59% of its original, uncompressed thickness), while the "stiff" variant of the foam undergoes compression of about 6% under that same applied pressure.

TABLE II

| RESILIENT ELEMENT TYPE | TOTAL APERTURE AREA - $MM^2$ | APERTURE COVER GAS PERMEABILITY - GM $H_2O/M^2/24$ HR | TIME FOR EXPANSION TO 90% OF ORIGINAL THICKNESS - MIN. |
|---|---|---|---|
| Stiff foam | 113 | 1500 | >30 |
| Stiff foam | 113 | 3700 | 17–20 |
| Soft foam | 226 | 3700 | 6–7 |
| Stiff foam | 226 | 3700 | 6 |

Preferably, at least end 508 of activator 502 is made from a substantially gas-impermeable material, such as those identified herein, to completely overlie aperture 222 and membrane 512 and to prevent the flow of air through the portion of semipermeable membrane 512 that overlies aperture 222. Activator 502 can be releasably adhesively connected with the wall of envelope 220, around aperture 222, by an annular area of pressure-sensitive adhesive 514 that completely surrounds aperture 222 and effectively isolates it from the ambient atmosphere until decompression of resilient element 215 is desired to commence. Thus, activator 502 completely overlies and covers both aperture 222 and semipermeable membrane 512 to prevent the flow of air through the portion of semipermeable membrane 512 that overlies aperture 222. Preferably, adhesive area 514 completely surrounds, but does not overlie, aperture 222, so that air can flow through semipermeable membrane 512 upon the peeling away of activator 502.

As shown in FIGS. 7 through 10, activator 502 includes an elongated element in the form of an elongated strip of substantially inextensible material. And in the form as shown in those drawing figures activator 502 has retention points defined by adhesive layers 506 and 510 that are offset laterally from each other, relative to the garment body. If desired, however, non-releasable adhesive layer 506 and releasable adhesive layer 510 can be in substantially overlying, opposed relationship, as shown in FIG. 10A, so that activator 502a is a shorter, folder-over element that extends between and is connected with opposed areas of envelope 220 and of secondary topsheet 43. In that embodiment, and as shown in FIG. 10A, non-releasable adhesive layer 500 that secures envelope 220 to topsheet 38 is preferably laterally spaced from non-releasable adhesive layer 506 a distance L so that the application of a tensile force to each of topsheet 38 and secondary topsheet 43 results in lateral relative movement between adhesive layer 500 and adhesive layer 506 to cause activator 502a to peel away from envelope 220. Distance L can be substantially the center-to-center distance between opposed portions of resilient element 215, or it can be between a distance that corresponds with the maximum width of envelope 220 and a distance that corresponds with the width of collection space 311.

Figure 11:
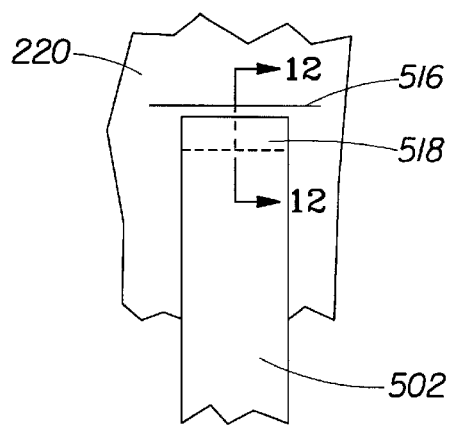
FIG. 11 is an enlarged, fragmentary plan view of a portion of an expandable-component-containing envelope, showing a connection between the expandable component envelope and the activator in which a line of weakness has been formed in a wall of the envelope.
Figure 12:
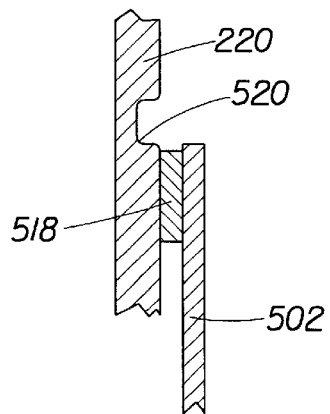
FIG. 12 is an enlarged, fragmentary cross-sectional view taken along the line 12—12 of FIG. 11, showing a score line formed in the envelope adjacent the activator.
Figure 13:
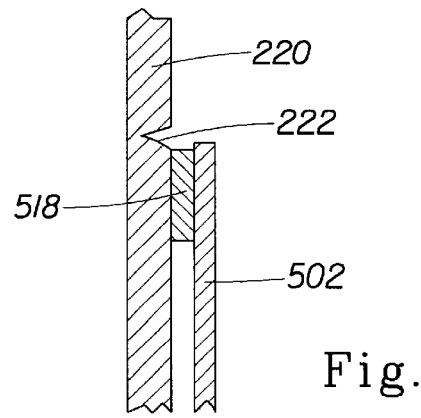
FIG. 13 is an enlarged, fragmentary cross-sectional view similar to that of FIG. 12, but showing a partial cut line provided in a wall of the envelope adjacent the activator.

In addition to allowing decompression of resilient element 215 by the opening of a pre-formed aperture 222 in envelope 220 by removing a covering member that overlies the aperture, air can also be allowed to enter envelope 220 by causing activator 502 to tear or rupture envelope 220 at a weakened area of the envelope wall. Referring now to FIGS. 11 through 13, envelope 220 includes a line of weakness 516 that is provided in the wall of envelope 220 adjacent the area at which activator 502 is attached thereto. As shown, activator 502 is securely non-releasably connected with envelope 220 at an attachment area 518, such as by an adhesive, by heat sealing, by ultrasonic welding, or the like. The location of attachment area 518 is closely adjacent line of weakness 516, preferably within about 2 cm therefrom, and most preferably within about 1 cm therefrom.

Line of weakness 516 can be in the form of a crease or a score line 520 that provides in the wall of envelope 220 a line of reduced wall thickness of predetermined length, as shown in FIG. 12. Score line 520 may be formed by pressing a scoring tool against the wall of envelope 220 and a suitable anvil surface underlying the wall of envelope 220, to locally compress and deform the envelope material and thereby provide a thin wall section that can readily be torn open by the application of a sufficient tensile force to activator 502, but that does not destroy the gas impermeability of envelope 220 until the necessary tensile force is applied. Preferably, the length of the score line is from about 0.5 cm to about 5 cm.

Alternatively, the line of weakness can be in the form of a cut line 522, as shown in FIG. 13. Cut line 522 extends only partially into the wall of envelope 220, to provide a thinner envelope wall section that defines the line of weakness. Cut line 522 has a predetermined length and defines a thin wall section at which a tear can be initiated in the wall of envelope 220 to provide an opening upon the application of a sufficient tensile force to activator 502, but that does not destroy the gas impermeability of envelope 220 until the necessary tensile force is applied. Preferably, the length of the cut line is from about 0.5 cm to about 5 cm.

In addition to the continuous score or cut line as shown in FIG. 11, line of weakness 516 can be a series of spaced, substantially aligned creases, scores, or cut lines.

Figure 14:
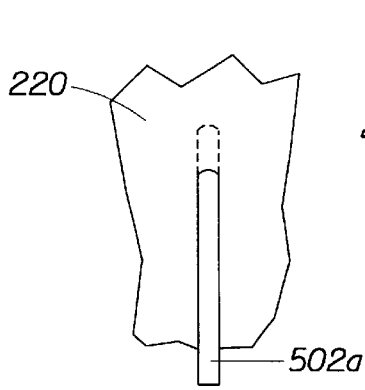
FIG. 14 is an enlarged, fragmentary plan view of another form of connection between an activator and an expandable-component-containing envelope in accordance with the present invention.

Referring to FIG. 14, instead of a flat strip connected to envelope 220 as shown in FIG. 11, activator 502 can be in the form of a thin rod 502a that extends through the envelope wall and into the interior of envelope 220. Activator rod 502a may be sealed directly to the part of the wall of envelope 220 through which it passes, to seal the envelope and to prevent the flow of air between activator 502a and the envelope wall. When the diaper is subjected to tension, activator 502a is pulled outwardly, relative to envelope 220, and is withdrawn from the envelope wall to thereby provide an opening in the wall through which air can flow. The size of the opening that results can be varied by changing the thickness or diameter of activator rod 502a, so that a larger thickness rod generally provides a larger size aperture.

Figure 15:
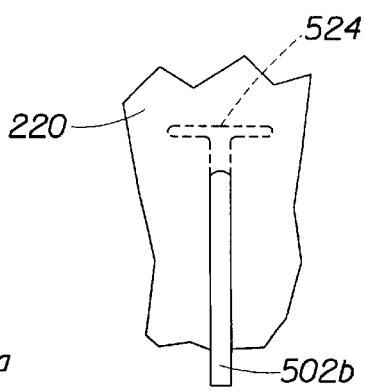
FIG. 15 is a view similar to that of FIG. 14, showing an activator having a T-shaped innermost end.
Figure 16:
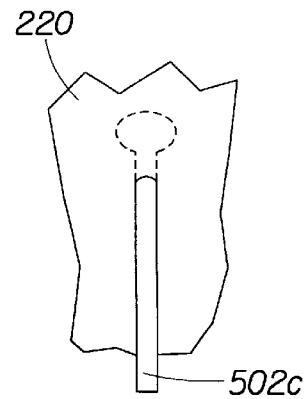
FIG. 16 is a view similar to that of FIG. 15, showing an activator having a rounded, bulbous innermost end.

Another way to control the size of the resulting aperture is to provide an enlarged portions such as innermost end on the activator. For example, transversely-extending T-member 524 at the innermost end of activator 502b, as shown in FIG. 15, or an enlarged end in the form of a bead 526, or the like, may be provided on a portion of the activator, as shown in FIG. 16. The transverse length of the T-member 524 and the size of bead 526 will influence the size of the aperture that is formed when the activator is pulled away from envelope 220.

It should be noted that the foregoing discussion directed to the use of a mechanical activator positioned internally within the garment has been in the context of the use of the activator in connection with the formation of an internal collection chamber for receiving and retaining fecal matter. However, it will be appreciated by those skilled in the art that the same structural elements and arrangements as are shown in FIGS. 7 through 16 can also be utilized and applied to activate front and rear waist region seals 400A and 400B and side margin seals 400C and 400D having the structure hereinbefore described. Moreover, although the foregoing description proceeds on the basis that envelope 220 is secured directly to absorbent core 44, to backsheet 42, or to topsheet 38, if desired the connection between envelope 220 to a structural element of the garment can be by an intermediate connection member, such as a connecting member or tether that extends from and is connected with the envelope and also with a structural element of the garment, such as topsheet 38 or secondary topsheet 43. And although disclosed as activated by the application of a tensile force in the longitudinal direction of the diaper, the elements can be so disposed as to be capable of activation by a tensile force in the transverse direction or any other direction, if desired. Further, it should be noted that the embodiments described herein are also applicable to training pant or brief type products with closed sides. In one such embodiment, the forces used to expand the product to slip over the hips could be used to actuate one or more expandable members. Examples of typical pull-on and training pant products are disclosed in U.S. Pat. Nos. 4,610,681; 4,938,753; 5,236,430; 5,569,234 and 5,836,932. The disclosure of each of these patents is incorporated by reference herein.

Figure 22:
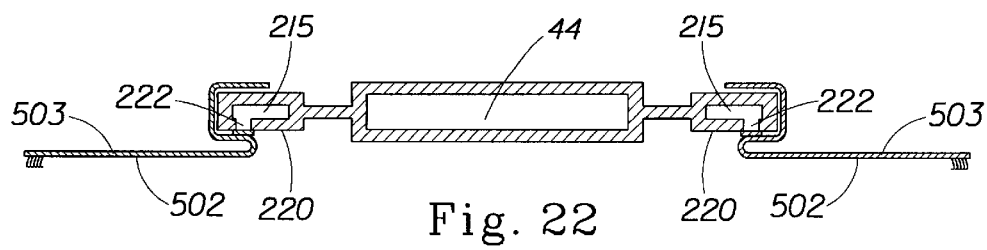
FIG. 22 is a cross-sectional view of an alternative embodiment of the present invention wherein the actuator is integral with the diaper.

Also, instead of a separate, elongated activator 502 that is attached to and that extends between a component of the garment and envelope 220, the activator can be integrally formed as a part of one component of the garment, such as the topsheet, the secondary topsheet, the absorbent core, or the backsheet. The first retention point can be a secure connection between envelope 220 and a component of the garment. The second retention point can be a secure connection between that same component and either an aperture cover, such as activator end 508 shown in FIGS. 7 and 8, or a secure connection with envelope 220 adjacent a line of weakness 516 as shown in FIG. 11. In that regard, the first and second retention points are connected with the envelope at spaced points that are movable away from each other by the application of tension to the garment, to provide an opening in envelope 220. In another alternative embodiment, as shown in FIG. 22, an integral portion of the diaper 20, such as side panel 503 can be used as the activator 502. The side panel 503 activator 502 is attached to the envelope 220 (which can also be an integral part of the diaper) in such a way that tensioning the side panel 503 pulls provides an opening 222 in the envelope. Once opened, the resilient member 215 is free to expand. It is contemplated that any part of the diaper 20 can be configured to act as the actuator 502 or envelope 220 and the present invention is not limited to the exemplary embodiment described herein.

Figure 17:
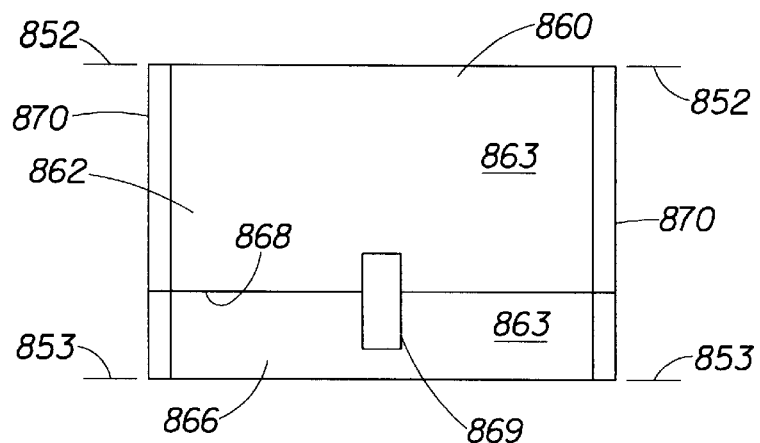
FIG. 17 is a front view of an individually wrapped and folded-over sanitary napkin.
Figure 18:
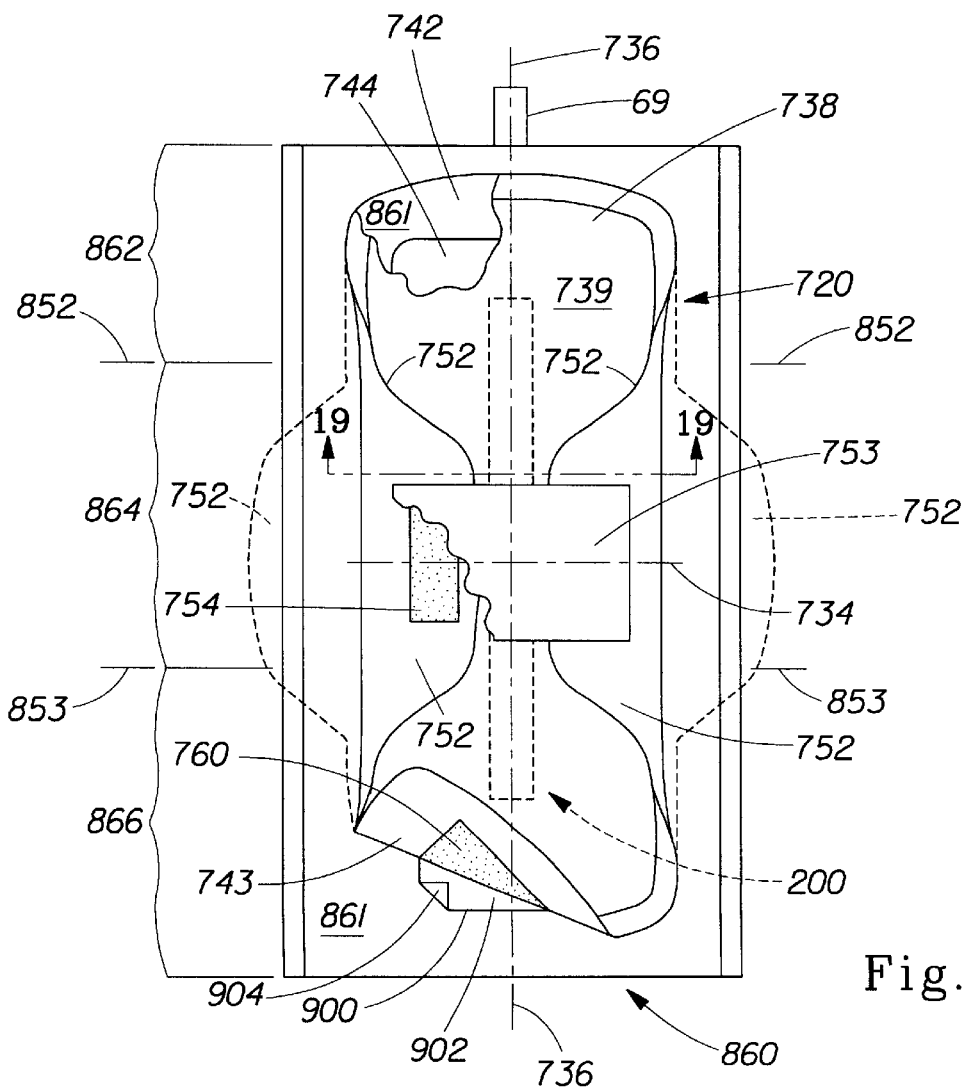
FIG. 18 is a top view of the sanitary napkin of FIG. 17, shown unfolded, and having an expandable component (shown in phantom) extending along the longitudinal centerline of the sanitary napkin.

FIGS. 17 through 20 show a sanitary napkin 720 incorporating an expansion member in accordance with the present invention. FIGS. 17 and 18 show a sanitary napkin 720 packaged in a flexible wrapper 860 that has an interior surface 861 and an exterior surface 863. Sanitary napkin 720 is joined to interior surface 861, which are folded as a unit with flexible wrapper 860 along two spaced fold lines 852 and 853. Fold lines 852 and 853 divide flexible wrapper 860 into panels 862, 864, and 866. Wrapper 860 and sanitary napkin 720 are shown in a closed, folded condition in FIG. 17, and in a fully unfolded condition in FIG. 18.

Wrapper 860 protects sanitary napkin 20 from becoming soiled prior to use and can be formed from various materials, including, but not limited to, paper, thermoplastic films, metallic foils, or laminates thereof. A suitable material from which flexible wrapper 860 can be formed is a polyethylene film having a thickness of about 0.025-millimeter (about one mil). Folded wrapper 860 can be sealed along package edges 870, such as by thermally or adhesively bonding together two or more of panels 862 to 866. A flap edge 868 of panel 862 can be joined to underlying panel 866 by a piece of adhesive tape 869.

Sanitary napkin 720 has a longitudinal centerline 736 and a lateral centerline 734 and includes a liquid pervious topsheet 738 having a body facing surface 739, a liquid impervious backsheet 742 joined with topsheet 738 and having a garment facing surface 743, and an absorbent core 744 positioned intermediate topsheet 738 and backsheet 742.

Figure 19:
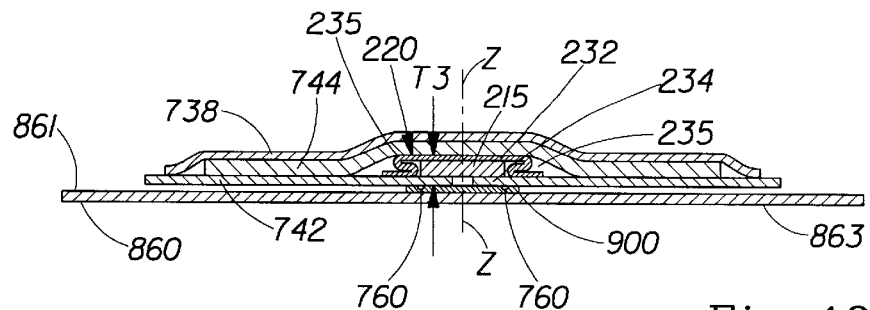
FIG. 19 is a cross-sectional view taken along the line 19—19 of FIG. 18 and showing the expandable component in a compressed condition.
Figure 20:
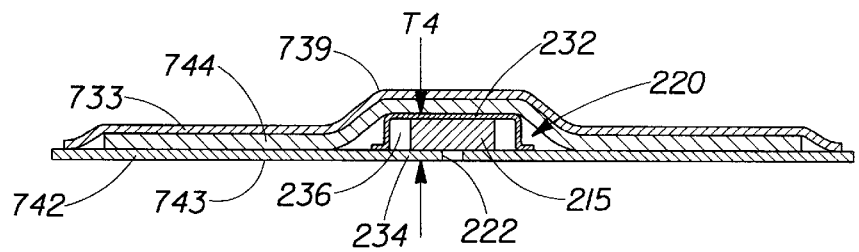
FIG. 20 is a cross-sectional view similar to that of FIG. 19 and showing the expandable component in an uncompressed condition.

Sanitary napkin 720 further includes an expandable component 200 (shown in phantom in FIG. 18). Expandable component 200 includes a compressed resilient element 215 disposed in a gas impermeable envelope 220, as shown in FIGS. 19 and 20. Expandable component 200 expands from a compressed configuration having a first Z-direction thickness T3, to an expanded configuration having a second Z-direction thickness T4 that is greater than first thickness T3. Expansion occurs upon the formation of an opening in air-impermeable envelope 220. Second thickness T4 is preferably at least about twice first thickness T3.

Expandable component 200 locally increases the Z-direction caliper of sanitary napkin 720. Both compressed and expanded configurations are shown in FIGS. 19 and 20, respectively. In expanded condition, expandable component 200 provides conformance of a portion of sanitary napkin 720 with the wearer's body to enhance acquisition and absorption of body exudates, and thereby to avoid the soiling of the wearer's undergarment.

While topsheet 738, backsheet 742, and absorbent core 744 can be assembled in a variety of well known configurations, suitable configurations are described generally in U.S. Pat. No. 5,007,906, which issued on Apr. 16, 1991, to Osborn et al.; U.S. Pat. No. 4,950,264, which issued on Aug. 21, 1990, to Osborn; U.S. Pat. No. 4,425,130, which issued on Jan. 10, 1984, to DesMarais; U.S. Pat. No. 4,321,924, which issued on Mar. 30, 1982, to Ahr; and U.S. Pat. No. 4,589,876, which issued on Aug. 18, 1987, to Van Tilburg. The disclosures of each of those patents are hereby incorporated herein by reference for purpose of generally describing assembly of components of a sanitary napkin 720.

Topsheet 738 is liquid pervious, permitting liquids to readily penetrate through its thickness. A suitable topsheet 738 can be manufactured from a wide range of materials, such as woven and nonwoven materials, polymeric materials such as apertured-formed thermoplastic films, and thermoplastic scrims. A suitable topsheet 738 can be an apertured formed film. Suitable apertured formed films are described in U.S. Pat. No. 3,929,135, which issued on Dec. 30, 1975, to Thompson; U.S. Pat. No. 4,324,246, which issued on Apr. 13, 1982, to Mullane et al.; U.S. Pat. No. 4,342,314, which issued on Aug. 3, 1982, to Radel et al.; U.S. Pat. No. 4,463,045, which issued on Jul. 31, 1984, to Ahr; and U.S. Pat. No. 5,006,394, which issued on Apr. 9, 1991, to Baird. The disclosures of each of those patents are hereby incorporated herein by reference.

A suitable formed film topsheet 738 is marketed on sanitary napkins by The Procter & Gamble Company, of Cincinnati, Ohio, as DRI-WEAVE. Body-facing surface 739 of topsheet 738 can be hydrophilic to enhance the transmission of body fluids through topsheet 738. A surfactant can be incorporated into the polymeric materials of formed film topsheet, or alternatively, body-facing surface 739 of the topsheet can be treated with a surfactant as described in above-identified U.S. Pat. No. 4,950,254 to Osborn.

Backsheet 742 is impervious to liquids and can be manufactured from a thin plastic film, although other flexible, liquid-impervious materials can be used. A suitable backsheet 742 is made from a polyethylene film having a thickness of from about 0.010 mm to about 0.051 mm. Suitable films from which backsheet 742 can be formed are manufactured by Clopay Corporation, of Cincinnati, Ohio, under the designation P18-0401, and by Ethyl Corporation, Visqueen Division, of Terre Haute, Ind., under the designation XP-39385.

Alternatively, one or both of topsheet 738 and backsheet 742 can be extensible, is and can be formed from an elastomeric or stretchable film. For example, backsheet 742 or portions of backsheet 742 can include a structural elastic-like film (SELF) web as described hereinabove. SELF webs suitable for the present invention are more completely described in copending, commonly assigned U.S. Pat. No. 5,518,801 entitled Web Materials Exhibiting Elastic-Like Behavior, which issued to Chappell, et, al. on May 21, 1996, the disclosure of which was earlier incorporated herein by reference.

Absorbent core 744 can be any absorbent means that is capable of absorbing or retaining liquids (e.g., menses, and/or urine). Absorbent core 744 can be manufactured in a wide variety of sizes and shapes (e.g., rectangular, oval, hourglass, etc.) and from a wide variety of liquid-absorbent materials, such as comminuted wood pulp, which is generally referred to as "airfelt." Other suitable absorbent materials include creped cellulose wadding; meltblown polymers; chemically stiffened, modified, or cross-linked cellulosic fibers; tissue, including tissue wraps and tissue laminates; absorbent foams; absorbent sponges; superabsorbent polymers; absorbent gelling materials, and combinations thereof. Suitable absorbent structures for use as absorbent core 744 of the present invention are described in U.S. Pat. No. 5,007,906, which issued on Apr. 16, 1991, to Osborn; U.S. Pat. No. 4,950,264, which issued on Aug. 21, 1990, to Osborn; U.S. Pat. No. 4,610,678, which issued on Sep. 9, 1986, to Weisman et al.; U.S. Pat. No. 4,834,735, which issued on May 30, 1989, to Alemany et al.; and European Patent Application No. 0 198 683, published Oct. 22, 1986, in the name of Duenk, et al. The disclosures of each of those patents are hereby incorporated herein by reference for purpose of showing suitable constructions and materials for absorbent core 744.

Sanitary napkin 720 can also include a pair of laterally extending flaps 752. Flaps 752 are configured to drape over the edges of the crotch region of the wearer's panty so that flaps 752 are disposed between the edges of wearer's panty and the thighs. Flaps 752 help prevent soiling of the wearer's body and panties by body exudates. Flaps 752 can include flap adhesive 754 for fastening flap 752 to the wearer's panty to thereby keep sanitary napkin 720 properly positioned within the panty. A piece of flap release paper 753 engages flap adhesive 754 on each flap 752, to hold flaps 752 in a folded position overlying topsheet 738 while sanitary napkin 720 is folded inside wrapper 860. Flaps 752 can be unfolded (as shown in phantom in FIG. (8) once release paper 753 is peeled from adhesive 754. The disclosures of the following U.S. Patents are hereby incorporated herein by reference for the purpose of showing sanitary napkin constructions having flaps 752: U.S. Pat. No. 4,950,264, which issued on Aug. 21, 1990, to Osborn; U.S. Pat. No. 4,589,876, which issued on May 20, 1986, to Van Tilburg; U.S. Pat. No. 4,608,047, which issued on Aug. 26, 1986, to Mattingly; U.S. Pat. No. 4,687,478, which issued on Aug. 18, 1987, to Van Tilburg; and U.S. Pat. No. 5,007,906, which issued on Apr. 16, 1991 to Osborn et al. Flaps 752 have been omitted from FIGS. 19 and 20 for purposes of clarity.

Sanitary napkin 720 can also include garment attachment adhesive 760 (see FIG. (8) for joining garment facing surface 743 of backsheet 742 to the wearer's panties. A strip of wrapper release paper 900 covers garment attachment adhesive 760 until the wearer is ready to fasten the sanitary napkin to the wearer's undergarment. A strip of release paper 900 has a first surface 902 and an oppositely facing surface 904. First surface 902 is joined to garment facing surface 743 of backsheet 742 by garment attachment adhesive 760, and second surface 904 of release paper 900 is joined to interior surface 861 of flexible wrapper 860 by wrapper adhesive. First surface 902 is preferably treated, such as with a coating including silicon, so that the adhesive bond between surface 902 and backsheet 742 has a lower strength than the adhesive bond between surface 904 and flexible wrapper 860. Such a bond strength difference is desirable so that release paper 900 stays joined to wrapper 860 when the consumer separates sanitary napkin 720 from wrapper 860.

Garment attachment adhesive 760 can include a pressure sensitive adhesive such as Century Adhesive A-305-IV manufactured by Century Adhesives Corporation, of Columbus, Ohio; adhesive Number 34-2823, manufactured by National Starch and Chemical Company, of Bridgewater, N.J.; and Fuller adhesive numbers HL-2238-XZP and HL-2254-XZP, manufactured by H. B. Fuller Company, of Vadnais Heights, Minn. A suitable release paper 900 is described in U.S. Pat. No. 4,917,697, which patent is hereby incorporated herein by reference. Another suitable release paper 900 is manufactured by Aerosol Corporation, of Menasha, Wis., as BL30MG-A Silox E1/O and BL30MG-A Silox 4P/O.

Referring to FIGS. 19 and 20, expandable component 200 includes a compressed resilient element 215 that is enclosed in a gas impermeable envelope 220 having two envelope walls 232 and 234. In FIGS. 19 and 20 envelope 220 is integral with backsheet 742, with wall 234 that is a portion of backsheet 742, and with wall 232 that is joined directly to a surface of backsheet 742. Alternatively, wall 234 can be formed from a piece of material separate from backsheet 742, if desired.

Walls 232 and 234 of envelope 220 are gas impermeable, and preferably they are made from a material that is soft and flexible. Suitable materials from which walls 232 and 234 can be made include thermoplastic films, such as a polyethylene film having a thickness of from about 0.010 mm to about 0.051 mm. Suitable polyethylene films are manufactured by Clopay Corp., of Cincinnati, Ohio, under designation P-18-1401, and by Tredegar Industries, of Terre Haute, Ind., under designations X8297 and HTS-5, FSII. Other suitable materials from which walls 232 and 234 can be made include RR8220 blown films and RR5475 cast films manufactured by Tredegar Industries.

In one embodiment, one or both of walls 232 and 234 can be formed from an elastomeric or stretchable film to accommodate expansion of resilient element 215. For example, one or both of walls 232 and 234 can include a SELF web as described in copending, commonly assigned U.S. patent application Ser. No. 08/203,456, entitled "Absorbent Article with Multiple Zone Structural Elastic-Like Film Web Extensible Waist Feature," filed by Donald C. Roe, et al. on Feb. 24, 1994, the disclosure of which is hereby incorporated herein by reference. It is noted that Application Ser. No. 08/203,456 matured into U.S. Pat. No. 5,554,145 issued on Sep. 10, 1996. Alternatively, one or both of walls 232 and 234 can be pre-formed, such as by vacuum forming, embossing, or folding, to accommodate expansion of resilient element 215. For example, one or both of walls 232 and 234 can have pleats for accommodating the expansion of resilient element 215. In FIG. 19 wall 232 is shown having longitudinally extending pleats 235.

Referring to FIGS. 19 and 20, the gas impermeable envelope can include an aperture 222 in a portion of backsheet 742 to which wrapper release paper 900 is adhesively joined. As shown in FIG. 19, release paper 900 covers aperture 222 and prevents air from entering cavity 236 between wall 232 and wall 234. Release paper 900 and garment attachment adhesive 760 form a releasable closure for covering aperture 222. When the consumer removes flexible wrapper 860 from sanitary napkin 720, release paper 900 remains adhered to wrapper 860. Aperture 222 is thereby uncovered, permitting expansion of compressed resilient element 215 within cavity 236, as shown in FIG. 20. In alternate embodiments, envelope 220 can include a resealable, releasable, closure-covering aperture 222. In yet another embodiment, aperture 222 can be omitted, and air impermeable envelope 220 can be opened by manually tearing walls 232 and 234 apart, as by cutting envelope 220 with a pair of scissors, by piercing envelope 220 with a lancet or simply removing the wrapper 860.

Resilient compressed element 215 is preferably porous, so that when releasable closure 250 is removed from aperture 222, expansion of resilient element 215 draws air into resilient element 215, as well as into the space within cavity 236 that is not occupied by resilient element 215. In one such embodiment, resilient element can include a porous sponge. In another embodiment resilient element 215 can include an open-cell foam, such as an open-cell polymeric foam. One suitable porous foam from which resilient element 215 can be made is a polyurethane foam, such as is available as #1230 foam from American Excelsior Corp., of Cincinnati, Ohio. Another suitable porous, open-cell foam is a foam prepared by polymerizing a high internal phase emulsion, such as is described in the above-identified U.S. Pat. No. 5,147,345, entitled "High Efficiency Absorbent Articles for Incontinence Management," that issued on Sep. 15, 1992 to Young et al.

Expandable component 200 can be disposed intermediate backsheet 742 and topsheet 738. In FIGS. 19 and 20, compressed resilient element 215 is positioned intermediate backsheet 742 and absorbent core 744. Compressed resilient element 215 thereby provides displacement of a portion of topsheet 738 and absorbent core 744, relative to backsheet 742, for enhanced acquisition of body exudates. Compressed resilient element 215 can extend along longitudinal centerline 736, as shown in phantom in FIG. 18. Resilient element 215 thereby convexly shapes a portion of body-facing surface 739 along longitudinal centerline 736, and increases the Z-direction thickness of sanitary napkin 720 along the longitudinal centerline to help conform topsheet 738 to wearer's body, particularly in the labial, perianal, and gluteal groove areas.

Although any suitable dimensions are possible, in one embodiment resilient element 215 may have a lateral width of between about 1.0 to about 2.0 centimeters and a free, unrestrained Z-direction thickness of between about 1.0 and about 2.0 centimeters prior to compression. In another embodiment, the Z-direction thickness of resilient element 215 can vary along the longitudinal centerline 736, thereby providing variations in the displacement of topsheet 738 and core 744 along the length of sanitary napkin 720, for selective fit in the labial, perianal, and gluteal groove areas of body.

Only one longitudinally extending resilient element 215 is shown in FIGS. 18 through 20. In other embodiments, the sanitary napkin can include multiple resilient elements 215. Resilient elements 215 can be disposed in separate or interconnected air impermeable envelopes 220. In the embodiment shown in FIGS. 19 and 20, resilient element 215 is disposed between backsheet 742 and topsheet 738. In yet another embodiment, the expandable component can be joined to garment facing surface 743 of sanitary napkin 720, to displace the sanitary napkin from the wearer's undergarment.

In the embodiments described above, resilient element 215 is disposed within an air impermeable envelope. In still another embodiment, resilient element 215 can be held in a compressed condition by an envelope that is either air permeable or air impermeable. For example, one or both of walls 232 and 234 can be air permeable, with adhesive spacing W2 (FIG. 21) sized so that walls 232 and 234 restrict expansion of resilient element 215. Resilient element 215 can be expanded at the point of use of the disposable absorbent article by removing a portion of the envelope holding resilient element 215 in a compressed condition. For example, resilient element 215 can be expanded by removing wall 232 from wall 234, such as by tearing or peeling.

Referring to FIG. 18, in yet another embodiment, the envelope holding resilient element 215 in a compressed condition can include wrapper 860. Resilient element 215 can be compressed as sanitary napkin 720 and wrapper 860 are folded as a unit about fold lines 852 and 853. Wrapper 860 is then sealed along edges 870 to maintain the compression of resilient element 215 within folded and sealed wrapper 860. Resilient element 215 can then expand when wrapper 860 is opened and is removed from sanitary napkin 720.

As will be appreciated by those skilled in the art, the activator structures and related structural elements and arrangements as are shown in FIGS. 7 through 16 can also be utilized and applied to the activation of sanitary napkin resilient elements.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable garment comprising:
   a. a garment body;
   b. a resilient, expansible member;
   c. a sealed envelope retained at a first retention point in the garment body and surrounding and enclosing the expansible member and maintaining the expansible member in an at least partially compressed condition; and
   d. an activator connected with the envelope at a first activator connection point and connected with the garment body at a second activator connection point that defines a second retention point spaced from the first retention point by a region of the garment body;
   whereby upon the application of a tensile force in a longitudinal or lateral direction to extend the region of the garment body between the first retention point and the second retention point, the activator opens a flow passageway into the envelope to admit air into the envelope and allow the expansible member to expand from its initial at least partially compressed condition to a substantially uncompressed condition.

2. A disposable garment in accordance with claim 1, wherein a portion of the garment is extensible at a force which is less than the force needed to extend the activator.

3. A disposable garment in accordance with claim 1, wherein the activator is substantially inextensible.

4. A disposable garment in accordance with claim 1, wherein the expansible member includes a foam material.

5. A disposable member in accordance with claim 4, wherein the foam material includes an open cell foam.

6. A disposable member in accordance with claim 1, wherein the expansible member defines a closed figure having an inner open space that defines an inner, collection volume when the expansible member is in a substantially uncompressed condition.

7. A disposable garment in accordance with claim 1, wherein the expansible member is of elongated, substantially rectilinear form.

8. A disposable garment in accordance with claim 1, wherein the expansible member is in the form of an open ended, substantially U-shaped member that defines an inner, collection volume when the expansible member is in a substantially uncompressed condition.

9. A disposable garment in accordance with claim 1, wherein the envelope is formed from a substantially gas-impervious material.

10. A disposable garment in accordance with claim 1, wherein the second activator connection point is an activator retention point that is defined by a non-releasable connection between the activator and the garment body.

11. A disposable garment in accordance with claim 1, wherein the envelope includes a pre-formed opening and the activator includes a sealing portion in overlying relationship with the opening to block flow of air through the opening.

12. A disposable garment in accordance with claim 11, wherein the opening has an area of from about 0.03 mm² to about 28.2 mm².

13. A disposable garment in accordance with claim 1, including a gas permeable film that extends over and covers the opening to limit the rate at which air can flow through the opening.

14. A disposable garment in accordance with claim 13, wherein the gas permeable film is selected from the group consisting of microporous films and monolithic films.

15. A disposable garment in accordance with claim 13, wherein the gas permeable film has a moisture vapor transmission rate of from about 500 gm $H_2O/m^2/24$ hr. to about 5000 gm $H_2O/m^2/24$ hr.

16. A disposable garment in accordance with claim 1, wherein the envelope includes a weakened area adjacent the first activator connection point.

17. A disposable garment in accordance with claim 1, wherein the envelope is attached to the garment body at a first retention point.

18. A disposable garment in accordance with claim 1, wherein the first retention point is a friction point which holds the envelope generally in place with respect to the garment body when the tensile force is applied.

19. A disposable garment in accordance with claim 16, wherein the weakened area is defined by a score line impressed into a wall of the envelope adjacent the first activator connection point.

20. A disposable garment in accordance with claim 16, wherein the weakened area is defined by a cut that extends partially into a wall of the envelope adjacent the first activator connection point.

21. A disposable garment in accordance with claim 1, wherein the envelope is connected with at least one structural element of the garment.

22. A disposable garment in accordance with claim 1, wherein the activator includes an end that extends into the envelope.

23. A disposable garment in accordance with claim 22, wherein the activator end includes an enlarged portion.

24. A disposable garment in accordance with claim 23, wherein the activator is generally T-shaped.

25. A disposable garment in accordance with claim 1, wherein the garment body includes a substantially liquid-impervious backsheet; a liquid pervious topsheet overlying and joined to the backsheet; and an absorbent core disposed between the topsheet and the backsheet.

26. A disposable garment in accordance with claim 25, wherein the disposable garment is a disposable diaper, training pant or a sanitary napkin.

27. A disposable garment in accordance with claim 25, wherein the expansible member is a spacer disposed between the topsheet and the backsheet for providing a fecal matter collection chamber.

28. A disposable garment in accordance with claim 25, wherein the topsheet includes an aperture through which fecal matter can pass, and wherein the expansible member defines a closed figure having an inner open space that is substantially in registry with the aperture in the topsheet.

29. A disposable garment in accordance with claim 25, wherein the diaper includes side margins, and wherein an expansible member is disposed in at least one of the side margins.

30. A disposable garment in accordance with claim 25, wherein the diaper includes front and rear waist regions, and wherein the expansible member is disposed in at least one of the waist regions.

31. A disposable garment in accordance with claim 25, wherein the diaper includes leg cuffs, and wherein the expansible member is disposed in at least one of the leg cuffs.

32. A disposable garment in accordance with claim 1, wherein the envelope is substantially evacuated of air so that the envelope remains in a substantially flattened condition with the expansible member in compressed form.

33. A disposable garment in accordance with claim 1, wherein the time within which expansible member decompresses from its initial at least partially compressed condition to a substantially uncompressed condition is less than 5 min. or between about 5 min. and about 20 min.

34. A sanitary napkin in accordance with claim 26, wherein the sanitary napkin includes a longitudinal axis and the expansible member is disposed along the longitudinal axis.

35. A disposable garment comprising:
   a. a first structural element;
   b. a second structural element;
   c. a sealed envelope connected with the first structural element at a first retention point and containing a resilient expansible member in an at least partially compressed condition; and
   d. an activator connected with the envelope and connected with the second structural element at a second retention point;
wherein upon the application of tension in a longitudinal or lateral direction to the garment, the first retention point and the second retention point move away from each other and the activator opens a flow passageway into the envelope to admit air into the envelope and allow the expansible member to expand from its at least partially compressed condition to a substantially uncompressed condition.

36. A disposable garment in accordance with claim 35 wherein the activator is integral with another element of the garment.

37. A disposable garment in accordance with claim 35 wherein the envelope is held in place between the first structural element and the second structural element within a pocket.

38. A disposable garment in accordance with claim 35 wherein the resilient expansible member is a spacer.

* * * * *

UNITED STATES PATENT AND TRADEMARK OFFICE
CERTIFICATE OF CORRECTION

PATENT NO. : 6,423,045 B1  
DATED : July 23, 2002  
INVENTOR(S) : Brandon E. Wise et al.

It is certified that error appears in the above-identified patent and that said Letters Patent is hereby corrected as shown below:

Title page,  
Item [56], References Cited, U.S. PATENT DOCUMENTS, add the following:

-- 3,881, 491  05/06/75  
  5,649,920  07/22/79 --.  
FOREIGN PATENT DOCUMENTS, add the following:

-- EP  0768070 A1  04/16/97  
  WO  95/00089  01/05/95 --.

Column 2,  
Line 65, delete "wom" and insert therefor -- worn --.

Column 5,  
Line 3, delete "composited" and insert therefor -- composted --.

Column 11,  
Line 13, delete the "is".

Signed and Sealed this

Thirteenth Day of July, 2004

JON W. DUDAS  
*Acting Director of the United States Patent and Trademark Office*